US008420636B2

(12) United States Patent
Behr et al.

(10) Patent No.: US 8,420,636 B2
(45) Date of Patent: Apr. 16, 2013

(54) PYRROLIDINYL-ALKYL-AMIDE DERIVATIVES, THEIR PREPARATION, AND THEIR THERAPEUTIC APPLICATION AS CCR3 RECEPTOR LIGANDS

(75) Inventors: Agnes Behr, Budapest (HU); Sandor Batori, Budapest (HU); Veronika Bartane Bodor, Budapest (HU); Zoltan Szlavik, Budapest (HU); Imre Bata, Budapest (HU); Katalin Urban-Szabo, Budapest (HU); Zoltan Kapui, Budapest (HU); Endre Mikus, Budapest (HU)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/014,145

(22) Filed: Jan. 26, 2011

(65) Prior Publication Data

US 2011/0144104 A1     Jun. 16, 2011

Related U.S. Application Data

(63) Continuation of application No. PCT/HU2009/000067, filed on Jul. 29, 2009.

(30) Foreign Application Priority Data

Jul. 31, 2008  (HU) .................................. 0800478

(51) Int. Cl.
| | | |
|---|---|---|
| C07D 513/04 | (2006.01) | |
| C07D 207/08 | (2006.01) | |
| C07D 417/14 | (2006.01) | |
| C07D 405/12 | (2006.01) | |
| A61K 31/4365 | (2006.01) | |
| A61K 31/496 | (2006.01) | |
| A61K 31/5377 | (2006.01) | |
| A61K 31/4025 | (2006.01) | |
| A61K 31/40 | (2006.01) | |

(52) U.S. Cl.
USPC ............... 514/234.2; 514/253.04; 514/301; 546/114; 544/127; 544/362; 548/517; 548/537

(58) Field of Classification Search ......................... None
See application file for complete search history.

(56) References Cited

U.S. PATENT DOCUMENTS 5,767,144 A     6/1998  Winn et al.
6,903,115 B2 *  6/2005  Rigby et al. .................. 514/316

FOREIGN PATENT DOCUMENTS

| WO | WO 03/082291 | 10/2003 |
|---|---|---|
| WO | WO 2004/076448 | 9/2004 |
| WO | WO 2004/084898 | 10/2004 |
| WO | WO 2007/034252 | 3/2007 |
| WO | WO 2007/034254 | 3/2007 |
| WO | WO 2010/013078 A3 | 2/2010 |

OTHER PUBLICATIONS

Zimmer, R. et al., Model Studies of the Reduction of 3-Phenyl-6H-1,2-Oxazines, Chemo- and Stereotselectivity: Synthesis of Amino Alcohols. Amino Acids, and Related Compounds, Chem. Ber., vol. 125, No. 10, pp. 2243-2248, (1992).
Anderson, A. G., et al., Azetidines. I. The Wittig Rearrangement of a 1-Benzylazetidine, J. Org. Chen., vol. 32, (1967), pp. 3241-3243.
Arshady, R., et al., Peptide Synthesis. Part 1. Preparation and Use of Polar Supports Based on Poly (Dimethylacrylamide), J. Chem. Soc. Perkin Trans. 1, (1981), pp. 529-537.
Bertrand, C. P., et al., CCR3 Blockade as a New Therapy for Asthma, Expert Opin. Invest. Drugs, (2000), vol. 9, No. 1, pp. 43-52.
Burckhalter, J. H., et al., Synthesis of Nicotine Analogs, J. Org. Chem., vol. 23, (1958), pp. 1281-1288.
Coste, J., et al., PyBop: A New Peptide Coupling Reagent Devoid of Toxic By-Product, Tetrahedron Letters, vol. 31, No. 2, pp. 205-208, (1990).
Elslager, E. F. et al., Folate Antagonists. 3. 2,4-Diamino-6-(Heterocyclic)Quinazolines, A Novel Class of Antimetabolites With Potent Antimalarial and Antibacterial Activity, Journal of Medicinal Chemistry, (1972), vol. 15, No. 8, pp. 827-836.
Elsner, J., et al., Chemokine Receptor Antagonists: A Novel Therapeutic Approach in Allergic Diseases, Allergy, (2004). vol. 59, pp. 1243-1258.
Faust, J. A., et al.. Antispasmodics: Esters of Heterocyclic Alcohols, JACS, (1959), vol. 81, pp. 2214-2218.
Hudson, D., et al., Methodological Implications of Simultaneous Solid-Phase Peptide Synthesis. 1. Comparison of Different Coupling Procedures, J. Org. Chem., (1988), vol. 53, pp. 617-624.
King, J. A., et al., The Preparation and Properties of Some B-Aminopropionic Acid Derivatives, JACS, (1946), vol.68, pp. 1468-1470.
Leplawy, M. T., et al., Peptides-XI Synthesis of Peptides Derived From Alpha-Methylalanine, Tetrahedron, (1960) vol. 11, pp. 39-51.
Pal, K., et al., A General Stereocontrolled Synthesis of Cis-2,3 Disubstituted Pyrrolidines and Piperidines, Tetrahedron Letters, vol. 34, No. 39, pp. 6205-6208.

(Continued)

*Primary Examiner* — Rebecca Anderson
*Assistant Examiner* — Michael Barker
(74) *Attorney, Agent, or Firm* — Ronald G. Ort

(57) ABSTRACT

The present invention relates to pyrrolidinyl-alkyl-amide derivatives of formula (I) or (IA)

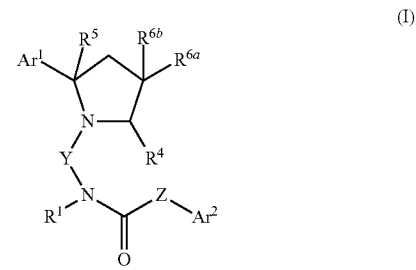

(I)

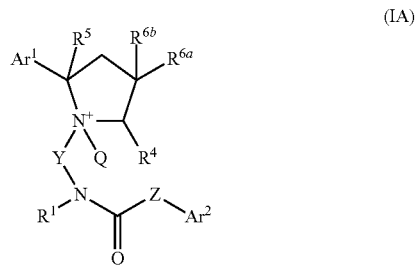

(IA)

wherein the variables are as defined herein, to their preparation and to their therapeutic use as CCR3 receptor ligands.

11 Claims, No Drawings

OTHER PUBLICATIONS

Roufos, I., et al., A Structure-Activity Relationship Study of Novel Phenylacetamides Which Are Sodium Channel Slackers, J. Med. Chem., (1996), vol. 39, pp. 1514-1520.

Shapiro, S.L., et. al., Aminoatkylamides and Oxazolidinediones, Journal of the American Chemical Society, vol. 81, No. 12, (1959), pp. 3083-3088.

Staab, H. A, et al., Reaktionsfahige Heterocyclische Diamide Der Kohlensaure1), Lieb. Ann. Chem., (1957), vol. 609, pp. 75-83.

Vaughan, J. R., et al., Acylalkylcarbonates as Acylating Agents for the Synthesis of Peptides, JACS, (1951), vol. 73, pp. 3547.

Weiland, V. T., et al., Uber Peptid-Synthesen. 3. Mitteilung1), J. Liebigs Ann. Chem., (1951). vol. 572, pp. 190-194.

Pailer, M., et al., Synthesen Von Verbindungen Mit Konstitutioneller Beziehung Zum Emetin, Monatsh. Chem., vol. 33, (1952), pp. 523-529.

\* cited by examiner

PYRROLIDINYL-ALKYL-AMIDE DERIVATIVES, THEIR PREPARATION, AND THEIR THERAPEUTIC APPLICATION AS CCR3 RECEPTOR LIGANDS

The present invention relates to the CCR3 receptor ligands of the general formula (I) or (IA), and to the salts and isomers thereof, to the pharmaceutical compositions containing them, to the use of the compounds of the general formula (I) and (IA), and their salts and isomers and to the preparation of the compounds of the general formula (I) and (IA), and their salts and isomers.

Chemokines are small molecular weight (8-12 kDa) secreted polypeptides playing important regulatory role in the immune processes due to their leukocyte attracting (chemotactic) effect. They exert their effects through the chemokine receptors, which belong to the family of the G protein coupled receptors.

The CC chemokine receptors 3 (CCR3 receptors) are expressed by a number of inflammatory cells, like the basophils, mast cells, T lymphocytes, epithelial cells, dendritic cells, but in the greatest amount they can be found on the surface of the eosinophils.

The CCR3 receptor ligands belong to the family of the C—C chemokines. They have a number of selective and non-selective ligands. The selective ligands are the eotaxin, eotaxin-2 and the lately discovered eotaxin-3. The non-selective ligands are the RANTES, the monocyte chemotactic proteins (MCP-2, MCP-3, MCP-4) and the macrophage inhibitor protein (MIP-1). The best characterized CCR3 ligand known from a long time is the eotaxin.

The eotaxin through the activation of the CCR3 receptors attracts selectively the eosinophils. Prior to an allergen provocation, the measured eotaxin level in the bronchoalveolar lavage fluid of asthmatic patients was by 67 percent higher. On the effect of provocation a 2.4-fold increase of the epithelial and endothelial cells of the respiratory tract were found.

In the lung the eotaxin is produced in many cells. Following an allergen response, the most important eotaxin sources are the epithelial cells, but a great amount of eotaxin is produced by the fibroblasts of the lung, the smooth muscle cells and the endothelial cells of the respiratory tract, the alveolar macrophages and lymphocytes, and the eosinophils themselves.

Originally the data showed that the CCR3 receptors are to find only in the eosinophil cells (Bertrand C P, Ponath P D., Expert Opin Investig Drugs. 2000 January; 9(1):43-52.), but on the basis of expression profiles it has been revealed that other inflammatory cells—although in smaller amount—also contain CCR3 receptors (Elsner J, Escher S E, Forssmann U., Allergy. 2004 December; 59(12):1243-58.). Thus, the CCR3 antagonists possess much wider effect, their activity is not limited to the eosinophils and consequently they can be considered much more valuable and effective targets in the treatment of allergic and inflammatory diseases.

Based on the above observations, CCR3 antagonists may possess important prophylactic and therapeutic effects in the treatment of pathologies where in the development of the disease CCR3 receptors play a role. These diseases are characterized by the disorder of the leukocyte functions (activation, chemotaxis), there are numerous chronic inflammatory diseases among them, such as asthma, allergic rhinitis, atopic dermatitis, eczema, inflammatory bowel disease, ulcerative colitis, Crohn's disease, allergic conjunctivitis, arthritis, multiple sclerosis, HIV-infection and diseases in conjunction with AIDS.

In the literature numerous CCR3 receptor antagonists have been published to date (e.g.: WO 03/082291, WO 2004/084898, WO 2004/076448, WO 2007/034252, WO 2007/034254). The present invention relates to a new structural type, the pyrrolidinyl-alkyl-amide derivatives. Representatives of these compounds are effective CCR3 receptor antagonists.

From the aspect of therapeutic use it is essential that the molecules do not bind, or bind only in case of very high concentration to other the CCR receptor subtypes.

Our aim was to prepare compounds of high antagonistic activity, and at the same time selective to the CCR3 receptor, i.e. which inhibit the CCR3 receptor in much smaller concentration as compared to other CCR receptors. Further aim was that the new compounds have stability, bioavailability, therapeutic index and toxicity values which ensure its drugability. Additional aim was that the compounds, through their good enteric absorption can be applied orally.

We have found that the compounds of the general formula (I) or (IA),

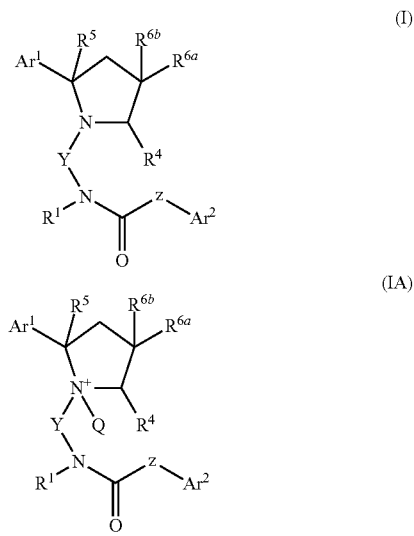

where

Ar$^1$ represents phenyl or naphthyl group—optionally substituted with one or more identical or non-identical straight or branched C$_{1-4}$ alkyl group, straight or branched C$_{1-4}$ alkoxy group, halogen atom, trifluoromethyl group, cyano group, nitro group, hydroxyl group, C$_{1-2}$ alkylenedioxy group, amino group, amino group substituted with one or two identical or non-identical straight or branched C$_{1-4}$ alkyl group;

R$^1$, represents hydrogen atom, or straight or branched C$_{1-4}$ alkyl group;

R$^4$, R$^5$, R$^{6a}$, R$^{6b}$ represents hydrogen atom, or

R$^4$ stands for straight or branched C$_{1-4}$ alkyl group and R$^5$, R$^{6a}$ and R$^{6b}$ represents hydrogen atom, or R$^5$ stands for straight or branched C$_{1-4}$ alkyl group and R$^4$, R$^{6a}$ and R$^{6b}$ represents hydrogen atom, or R$^{6a}$ stands for straight or branched C$_{1-4}$ alkyl group and R$^{6b}$ stands for straight or branched C$_{1-4}$ alkyl group or hydrogen atom and R$^5$, R$^4$ represent hydrogen atom;

Y, Z independently represent straight C$_{1-4}$ alkylene group—optionally substituted with one or more identical or non-identical straight or branched C$_{1-4}$ alkyl group;

Ar² represents a phenyl-, thienyl-, or furyl group,—optionally substituted with one or more, identical or non-identical, straight or branched $C_{1-4}$ alkyl group, straight or branched $C_{1-4}$ alkoxy group, halogen atom, hydroxyl group, cyano group, nitro group, trifluoromethyl group, $C_{1-2}$ alkylenedioxy group, amino group, or amino group substituted with one or two identical or non-identical straight or branched $C_{1-4}$ alkyl group; or 5- or 6-membered heterocyclic ring containing one, two, or three nitrogen atoms, or one nitrogen atom and one oxygen atom, or one nitrogen atom and one sulfur atom—optionally substituted with one or more, identical or non-identical, straight or branched $C_{1-4}$ alkyl group, straight or branched $C_{1-4}$ alkoxy group, hydroxyl group, halogen atom, nitro group, cyano group, trifluoromethyl group, $C_{1-2}$ alkylenedioxy group, $-NR^7R^8$, $-CONR^7R^8$ or $-SO_2NR^7R^8$ group—where $R^7$ and $R^8$ independently stand for hydrogen atom, straight or branched $C_{1-4}$ alkyl group, or $R^7$ and $R^8$ together with the nitrogen atom form a group of general formula (a),

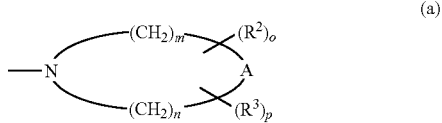

(a)

where,
$R^2$, $R^3$ represent straight or branched $C_{1-4}$ alkyl group or $C_{3-6}$ cycloalkyl group,
A represents $-CHR^{12}$ group, oxygen atom, sulfur atom or $-NR^9$ group—where $R^{12}$ and $R^9$ stand for hydrogen atom, straight or branched $C_{1-4}$ alkyl group or $C_{3-6}$ cycloalkyl group—,
m has the value of 1, 2 or 3,
n has the value of 1 or 2,
o has the value of 0 or 1,
p has the value of 0 or 1;
or
the benzolog of a 5- or 6-membered heterocyclic ring containing one, two, or three nitrogen atoms, or one nitrogen atom and one oxygen atom, or one nitrogen atom and one sulfur atom—optionally substituted with one or more, identical or non-identical, straight or branched $C_{1-4}$ alkyl group, straight or branched $C_{1-4}$ alkoxy group, hydroxyl group, halogen atom, trifluoromethyl group, nitro group, cyano group, $C_{1-2}$ alkylenedioxy group, $-NR^7R^8$, $-CONR^7R^8$ or $-SO_2NR^7R^8$ group—where the meanings of $R^7$ and $R^8$ are as defined above; or
the derivative of a 5- or 6-membered heterocyclic ring containing one, two, or three nitrogen atoms, or one nitrogen atom and one oxygen atom, or one nitrogen atom and one sulfur atom, condensed with heteroaromatic 6-membered rings containing one or two nitrogen atoms—optionally substituted with one or more, identical or non-identical, straight or branched $C_{1-4}$ alkyl group, straight or branched $C_{1-4}$ alkoxy group, hydroxyl group, halogen atom, nitro group, cyano group, trifluoromethyl group, $C_{1-2}$ alkylenedioxy group, $-NR^7R^8$, $-CONR^7R^8$ or $-SO_2NR^7R^8$ group—where the meanings of $R^7$ and $R^8$ are as defined above;
Q represents $-O^-$ group, $-N^-$$-H$ or $-N^-$$-CO-R^{10}$ group—where $R^{10}$ stands for hydrogen atom, straight or branched $C_{1-4}$ alkyl group, $C_{3-6}$ cycloalkyl group, phenyl-, benzyl- or $-NH-R^{11}$-group—where $R^{11}$ represents straight or branched $C_{1-4}$ alkyl group, $C_{3-6}$ cycloalkyl group, phenyl- or benzyl-group—;
and their salts and isomers and the salts thereof, fulfill the above criteria.

The detailed meanings of the above substituents are as follows:

By a $C_{1-4}$ alkyl group we mean a saturated straight- or branched-chain aliphatic group of 1-4 carbon atoms, such as methyl-, ethyl-, propyl-, isopropyl-, butyl-, isobutyl-, secondary butyl-, tertiary butyl group.

By a $C_{1-4}$ alkylene group we mean a $-(CH_2)_n-$ group where the value of n is 1, 2, 3 or 4, such as a methylene-, ethylene-, propylene-, butylene group.

By a $C_{3-6}$ cycloalkyl group we mean a cyclic alkyl group of 3-6 carbon atoms, such as cyclopropyl-, cyclobutyl-, cyclopentyl- or cyclohexyl-group.

By a $C_{1-4}$ alkoxy group we mean an $-O-(C_{1-4}$ alkyl group)—where the meaning of alkyl is as defined above-, such as methoxy-, ethoxy-, propoxy-, isopropoxy-, butoxy-, isobutoxy-, secondary butoxy- or tertiary butoxy group.

By a $C_{1-2}$ alkylenedioxy group we mean an $-O$-alkylene-$O-$ group, where the meaning of alkylene is as defined above—such as methylenedioxy- or ethylenedioxy-group.

By halogen atom we mean chloro, fluoro, iodo or bromo atom.

A 5- or 6-membered heterocyclic ring containing one, two or three nitrogen atoms may mean an unsaturated, saturated or partially saturated heterocyclic ring, for example pyrrole, imidazole, pyrazole, 1,2,3-triazole, 1,2,4-triazole, pyridine, pyrimidine, pyridazine, pyrazine, 1,2,4-triazine, 1,3,5-triazine, 1,2,3-triazine, pyrrolidine, imidazolidine, [1,2,4]-triazolidine, piperidine, piperazine, 2-imidazoline ring.

A 5- or 6-membered heterocyclic ring containing one nitrogen atom and one oxygen or sulfur atom may mean an unsaturated, saturated or partially saturated heterocyclic ring, as for example oxazole, isoxazole, thiazole, isothiazole, 1,2-oxazine, 1,3-oxazine, 1,4-oxazine, 1,2-thiazine, 1,3-thiazine, 1,4-thiazine, oxazolidine, thiazolidine, morpholine, thiomorpholine, 2-thiazoline, 2-oxazoline ring.

By benzolog we mean derivatives condensed with benzene ring, for example indole, benzoxazole, benzothiazole, benzimidazole, quinoline, quinazoline, quinoxaline.

The condensed derivatives of a 5- or 6-membered heterocyclic ring—containing one, two or three nitrogen atoms, or one nitrogen atom and one oxygen atom, or one nitrogen atom and one sulfur atom—condensed with 6-membered heteroaromatic rings—containing one or two nitrogen atom—, may for example be a thiazolopyridine, triazolopyridine, thiazolopyrimidine, thiazolopyrazine, oxazolopyridine, 9H-purine, 3H-imidazopyridine.

The group of the general formula (a) preferably represents a pyrrolidino-, piperidino-, morpholino-, piperazino-, 4-methylpiperazino-, 2,6-dimethylmorpholino-group.

By salts of the compounds of general formula (I) or (IA) we mean salts given with inorganic and organic acids and bases. Preferred are the salts formed with pharmaceutically acceptable acids, e.g. hydrochloric acid, sulfuric acid, ethanesulfonic acid, tartaric acid, fumaric acid, citric acid.

By isomers we mean structural and optical isomers. Structural isomers may be tautomeric forms in equilibrium, or isolated desmotrops, which are also subjects of the invention. The compounds of general formula (I) or (IA) may contain one or more asymmetric carbon atom, thus they may be optical isomers, enantiomers or diastereoisomers. These enantiomers and diastereoisomers and the mixtures thereof, including the racemates, are also subjects of the invention.

A narrower group of the compounds of general formula (IA) is formed by those, where $Ar^1$ represents phenyl or naphthyl group—optionally substituted with one or more identical or non-identical straight or branched $C_{1-4}$ alkyl group, straight or branched $C_{1-4}$ alkoxy group, halogen atom, trifluoromethyl group, cyano group, nitro group, hydroxyl group, $C_{1-2}$ alkylenedioxy group, amino group, or amino group substituted with one or two identical or non-identical straight or branched $C_{1-4}$ alkyl group;

$R^1$, represents hydrogen atom, or straight or branched $C_{1-4}$ alkyl group;

$R^4$, $R^5$, $R^{6a}$, $R^{6b}$ represent hydrogen atom, or
  $R^4$ stands for straight or branched $C_{1-4}$ alkyl group and $R^5$, $R^{6a}$ and $R^{6b}$ represent hydrogen atom, or
  $R^5$ stands for straight or branched $C_{1-4}$ alkyl group and $R^4$, $R^{6a}$ and $R^{6b}$ represent hydrogen atom, or
  $R^{6a}$ stands for straight or branched $C_{1-4}$ alkyl group and $R^{6b}$ stands for straight or branched $C_{1-4}$ alkyl group or hydrogen atom and $R^5$, $R^4$ represent hydrogen atom;

Y, Z independently represent straight $C_{1-4}$ alkylene group—optionally substituted with one or more identical or non-identical straight or branched $C_{1-4}$ alkyl group;

$Ar^2$ represents a phenyl-, thienyl-, or furyl group,—optionally substituted with one or more identical or non-identical straight or branched $C_{1-4}$ alkyl group, straight or branched $C_{1-4}$ alkoxy group, halogen atom, hydroxyl group, cyano group, nitro group, trifluoromethyl group, $C_{1-2}$ alkylenedioxy group, amino group, or amino group substituted with one or two identical or non-identical straight or branched $C_{1-4}$ alkyl group; or 5- or 6-membered heterocyclic ring containing one, two, or three nitrogen atoms, or one nitrogen atom and one oxygen atom, or one nitrogen atom and one sulfur atom—optionally substituted with one or more identical or non-identical straight or branched $C_{1-4}$ alkyl group, straight or branched $C_{1-4}$ alkoxy group, hydroxyl group, halogen atom, nitro group, cyano group, trifluoromethyl group, $C_{1-2}$ alkylenedioxy group, —$NR^7R^8$, —$CONR^7R^8$ or —$SO_2NR^7R^8$ group—where $R^7$ and $R^8$ independently stand for hydrogen atom, straight or branched $C_{1-4}$ alkyl group or $R^7$ and $R^8$ together with the nitrogen atom form a group of general formula (a),

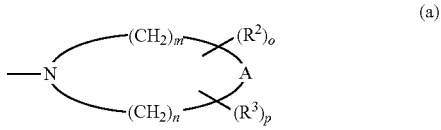

(a)

where,
$R^2$, $R^3$ represent straight or branched $C_{1-4}$ alkyl group or $C_{3-6}$ cycloalkyl group,
A represents —$CHR^{12}$ group, oxygen atom, sulfur atom or —$NR^9$ group—where $R^{12}$ and $R^9$ stand for hydrogen atoms, straight or branched $C_{1-4}$ alkyl group or $C_{3-6}$ cycloalkyl group—,
m has the value of 1, 2 or 3,
n has the value of 1 or 2,
o has the value of 0 or 1,
p has the value of 0 or 1;
or
the benzolog of a 5- or 6-membered heterocyclic ring containing one, two, or three nitrogen atoms, or one nitrogen atom and one oxygen atom, or one nitrogen atom and one sulfur atom—optionally substituted with one or more identical or non-identical straight or branched $C_{1-4}$ alkyl group, straight or branched $C_{1-4}$ alkoxy group, hydroxyl group, halogen atom, trifluoromethyl group, nitro group, cyano group, $C_{1-2}$ alkylenedioxy group, —$NR^7R^8$,—$CONR^7R^8$ or —$SO_2NR^7R^8$ group—where the meanings of $R^7$ and $R^8$ are as defined above—; or the derivative of a 5- or 6-membered heterocyclic ring containing one, two, or three nitrogen atoms, or one nitrogen atom and one oxygen atom, or one nitrogen atom and one sulfur atom, condensed with heteroaromatic 6-membered rings containing one or two nitrogen atoms,—optionally substituted with one or more identical or non-identical straight or branched $C_{1-4}$ alkyl group, straight or branched $C_{1-4}$ alkoxy group, hydroxyl group, halogen atom, nitro group, cyano group, trifluoromethyl group, $C_{1-2}$ alkylenedioxy group, —$NR^7R^8$, —$CONR^7R^8$ or —$SO_2NR^7R^8$ group—where the meanings of $R^7$ and $R^8$ are as defined above;

Q represents —$N^-$—H group;
and their salts and isomers and the salts thereof.

Another narrower group of the compounds of general formula (I) or (IA) is formed by those,
where
$Ar^1$ represents phenyl or naphthyl group—optionally substituted with one or more identical or non-identical straight or branched $C_{1-4}$ alkyl group, straight or branched $C_{1-4}$ alkoxy group, halogen atom;

$R^1$ represents hydrogen atom, or methyl group;
$R^4$, $R^5$, $R^{6a}$, $R^{6b}$ represent hydrogen atom, or
  $R^4$ stands for methyl group and $R^5$, $R^{6a}$ and $R^{6b}$ represent hydrogen atom, or
  $R^5$ stands for methyl group and $R^4$, $R^{6a}$ and $R^{6b}$ represent hydrogen atom, or
  $R^{6a}$ stands for methyl group and $R^{6b}$ stands for methyl group or hydrogen atom and
  $R^5$, $R^4$ represent hydrogen atom;

Y, Z independently represent straight $C_{1-4}$ alkylene group—optionally substituted with one or more identical or non-identical straight or branched $C_{1-4}$ alkyl group;

$Ar^2$ represents the benzolog of a 5- or 6-membered heterocyclic ring containing one, two, or three nitrogen atoms, or one nitrogen atom and one oxygen atom, or one nitrogen atom and one sulfur atom—optionally substituted with one or more identical or non-identical straight or branched $C_{1-4}$ alkyl group, straight or branched $C_{1-4}$ alkoxy group, hydroxyl group, halogen atom, trifluoromethyl group, nitro group, cyano group, $C_{1-2}$ alkylenedioxy group, —$NR^7R^8$, —$CONR^7R^8$ or —$SO_2NR^7R^8$ group—where $R^7$ and $R^8$ independently mean hydrogen atom, straight or branched $C_{1-4}$ alkoxy group, or $R^7$ and $R^8$ together with the nitrogen atom form a group of the general formula (a),

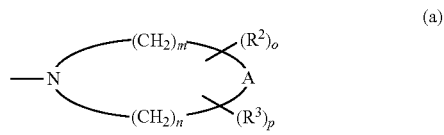

(a)

where,
$R^2$, $R^3$ represent straight or branched $C_{1-4}$ alkyl group or $C_{3-6}$ cycloalkyl group, A represents —CHR$^{12}$ group, oxygen atom, sulfur atom or —NR$^9$ group—where R$^{12}$ and R$^9$ stand for hydrogen atom, straight or branched C$_{1-4}$ alkyl group or C$_{3-6}$ cycloalkyl group—,
m has the value of 1, 2 or 3,
n has the value of 1 or 2,
o has the value of 0 or 1,
p has the value of 0 or 1,—
or
the derivative of a 5- or 6-membered heterocyclic ring containing one, two, or three nitrogen atoms, or one nitrogen atom and one oxygen atom, or one nitrogen atom and one sulfur atom, condensed with heteroaromatic 6-membered rings containing one or two nitrogen atoms—optionally substituted with one or more identical or non-identical straight or branched C$_{1-4}$ alkyl group, straight or branched C$_{1-4}$ alkoxy group, hydroxyl group, halogen atom, nitro group, cyano group, trifluoromethyl group, C$_{1-2}$ alkylenedioxy group, —NR$^7$R$^8$, —CONR$^7$R$^8$ or —SO$_2$NR$^7$R$^8$ group—where the meanings of R$^7$ and R$^8$ are as defined above;
Q represents —O$^-$ group, —N$^-$—H or —N$^-$—CO—R$^{10}$ group—where R$^{10}$ stands for hydrogen atom, straight or branched C$_{1-4}$ alkyl group, C$_{3-6}$ cycloalkyl group, phenyl-, benzyl- or —NH—R$^{11}$ group—where R$^{11}$ represents straight or branched C$_{1-4}$ alkyl group, C$_{3-6}$ cycloalkyl group, phenyl- or benzyl-group—;
and their salts and isomers and the salts thereof.
A further narrower group of the compounds of general formula (I) or (IA) is formed by those,
where
Ar$^1$ represents phenyl group—optionally substituted with one or more identical or non-identical halogen atom;
R$^1$ represents hydrogen atom;
R$^4$, R$^5$, R$^{6a}$, R$^{6b}$ represent hydrogen atom;
Y, Z independently represent straight C$_{1-4}$ alkylene group—optionally substituted with one or more identical or non-identical straight or branched C$_{1-4}$ alkyl group;
Ar$^2$ represents the benzolog of a 5- or 6-membered heterocyclic ring containing one nitrogen atom and one sulfur atom—optionally substituted with one or more identical or non-identical straight or branched C$_{1-4}$ alkyl group, or the derivative of a 5- or 6-membered heterocyclic ring containing one nitrogen atom and one sulfur atom, condensed with heteroaromatic 6-membered rings containing one or two nitrogen atoms—optionally substituted with one or more identical or non-identical straight or branched C$_{1-4}$ alkyl group, straight or branched C$_{1-4}$ alkoxy group, —NR$^7$R$^8$ group—where R$^7$ and R$^8$ independently mean hydrogen atom, straight or branched C$_{1-4}$ alkyl group or R$^7$ and R$^8$ together with the nitrogen atom form a group of the general formula (a);

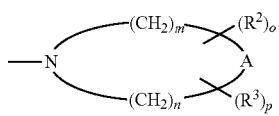

(a)

where,
R$^2$, R$^3$ represent straight or branched C$_{1-4}$ alkyl group or C$_{3-6}$ cycloalkyl group,
A represents —CHR$^{12}$ group, oxygen atom, sulfur atom or —NR$^9$ group—where R$^{12}$ and R$^9$ stand for hydrogen atom, straight or branched C$_{1-4}$ alkyl group or C$_{3-6}$ cycloalkyl group—,
m has the value of 1, 2 or 3,
n has the value of 1 or 2,
o has the value of 0 or 1,
p has the value of 0 or 1;
Q represents —O$^-$ group, —N$^-$—H or —N$^-$—CO—R$^{10}$ group—where R$^{10}$ stands for hydrogen atom, straight or branched C$_{1-4}$ alkyl group, or —NH—R$^{11}$ group—where R$^{11}$ represents straight or branched C$_{1-4}$ alkyl group—;
and their salts and isomers and the salts thereof.
A further narrower group of the compounds of general formula (I) or (IA) is formed by those,
where
Ar$^1$ represents phenyl group substituted with one or two identical or non-identical halogen atom,
and the meaning of R$^1$, R$^4$, R$^5$, R$^{6a}$, R$^{6b}$, Y, Z, Ar$^2$ and Q is as defined above,
and their salts- and isomers and the salts thereof.
An even narrower group of the compounds of the general formula (I) or (IA) is formed by the following compounds:
N-{3-[2-(3,4-dichlorophenyl)pyrrolidin-1-yl]propyl}-3-(5-methoxy[1,3]thiazolo[5,4-b]pyridin-2-yl)propionamide,
N-{3-[2-(3,4-dichlorophenyl)pyrrolidin-1-yl]propyl}-3-(5-(methylamino) [1,3]thiazolo[5,4-b]pyridin-2-yl)propionamide,
N-{3-[2-(3,4-dichlorophenyl)pyrrolidin-1-yl]propyl}-3-(5-pyrrolidin-1-yl[1,3]thiazolo[5,4-b]pyridin-2-yl)propionamide,
N-{3-[2-(3,4-dichlorophenyl)pyrrolidin-1-yl]propyl}-3-(5-piperidin-1-yl[1,3]thiazolo[5,4-b]pyridin-2-yl)propionamide,
N-{3-[2-(3,4-dichlorophenyl)pyrrolidin-1-yl]propyl}-3-(5-morpholin-4-yl[1,3]thiazolo[5,4-b]pyridin-2-yl)propionamide,
N-{3-[2-(3,4-dichlorophenyl)pyrrolidin-1-yl]propyl}-3-(5-methyl[1,3]thiazolo[5,4-b]pyridin-2-yl)propionamide,
N-{3-[2-(3,4-dichlorophenyl)pyrrolidin-1-yl]propyl}-3-(5-(4-methylpiperazin-1-yl)[1,3]thiazolo[5,4-b]pyridin-2-yl)propionamide,
N-{3-[2-(3,4-dichlorophenyl)pyrrolidin-1-yl]propyl}-3-(6-methyl-1,3-benzothiazol-2-yl)propionamide,
N-{3-[2-(3,4-dichlorophenyl)pyrrolidin-1-yl]propyl}-3-(5-(2,6-dimethylmorpholin-4-yl)[1,3]thiazolo[5,4-b]pyridin-2-yl)propionamide,
N-{3-[2-(3,4-dichlorophenyl)pyrrolidin-1-yl]propyl}-3-(6-piperidin-1-yl)[1,3]thiazolo[4,5-b]pyrazin-2-yl)propionamide,
N-{3-[2-(3,4-dichlorophenyl)pyrrolidin-1-yl]propyl}-3-(6-morpholin-4-yl) [1,3]thiazolo[4,5-b]pyrazin-2-yl)propionamide,
N-(3-[2-(3,4-dichlorophenyl)pyrrolidin-1-yl]-1-methylpropyl)-3-(5-morpholin-4-yl[1,3]thiazolo[5,4-b]pyridin-2-yl)]propionamide,
N-(3-[2-(3,4-dichlorophenyl)pyrrolidin-1-yl]-1-methylpropyl)-3-(5-piperidin-1-yl[1,3]thiazolo[5,4-b]pyridin-2-yl)]propionamide,
1-amino-2-(3,4-dichlorophenyl)-1-(3-{[3-(5-pyrrolidin-1-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-morpholin-4-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-methyl[1,3]thiazolo[4,5-b]pyridin-2-yl)propanoyl]amino}propyl)pyrrolidinium tosylate, 1-amino-2-(3,4-dichlorophenyl)-1-[3-({3-(5-(2,6-dimethyl-morpholin-4-yl)[1,3]thiazolo[4,5-b]pyridin-2-yl)propanoyl]amino}propyl)pyrrolidinium tosylate, N-{3-[2-(3,4-dichlorophenyl)-1-oxidopyrrolidin-1-yl]propyl}-3-(5-piperidin-1-yl)[1,3]thiazolo[4,5-b]pyridin-2-yl)propionamide, N-{3-[2-(3,4-dichlorophenyl)-1-oxidopyrrolidin-1-yl]propyl}-3-(5-morpholin-4-yl[1,3]thiazolo[4,5-b]pyridin-2-yl)propionamide, N-{3-[2-(3,4-dichlorophenyl)-1-oxidopyrrolidin-1-yl]propyl}-3-(5-pyrrolidin-1-yl[1,3]thiazolo[4,5-b]pyridin-2-yl)propionamide, 1-(Acetylamino)-2-(3,4-dichlorophenyl)-1-(3-{[3-(5-piperidin-1-yl[1,3]thiazolo[4,5-b]pyridin-2-yl)propanoyl]amino}propyl)pyrrolidinium hydrochloride and their salts and isomers and the salts thereof.

An even narrower group of the compounds of the general formula (I) or (IA) is formed by the following compounds:

N-{3-[2-(3,4-dichlorophenyl)pyrrolidin-1-yl]propyl}-3-(5-(methylamino) [1,3]thiazolo[5,4-b]pyridin-2-yl)propionamide N-{3-[2-(3,4-dichlorophenyl)pyrrolidin-1-yl]propyl}-3-(5-pyrrolidin-1-yl[1,3]thiazolo[5,4-b]pyridin-2-yl)propionamide N-{3-[2-(3,4-dichlorophenyl)pyrrolidin-1-yl]propyl}-3-(5-piperidin-1-yl[1,3]thiazolo[5,4-b]pyridin-2-yl)propionamide N-{3-[2-(3,4-dichlorophenyl)pyrrolidin-1-yl]propyl}-3-(5-morpholin-4-yl[1,3]thiazolo[5,4-b]pyridin-2-yl)propionamide, N-{3-[2-(3,4-dichlorophenyl)pyrrolidin-1-yl]propyl}-3-(5-(2,6-dimethylmorpholin-4-yl)[1,3]thiazolo[5,4-b]pyridin-2-yl)propionamide, 1-amino-2-(3,4-dichlorophenyl)-1-(3-{[3-(5-pyrrolidin-1-yl[1,3]thiazolo[4,5-b]pyridin-2-yl)propanoyl]amino}propyl)pyrrolidinium tosylate, 1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate, 1-amino-2-(3,4-dichlorophenyl)-1-(3-{[3-(5-morpholin-4-yl[1,3]thiazolo[4,5-b]pyridin-2-yl)propanoyl]amino}propyl)pyrrolidinium tosylate, 1-amino-2-(3,4-dichlorophenyl)-1-(3-{[3-(5-methyl[1,3]thiazolo[4,5-b]pyridin-2-yl)propanoyl]amino}propyl)pyrrolidinium tosylate, 1-amino-2-(3,4-dichlorophenyl)-1-[3-({3-(5-(2,6-dimethyl-morpholin-4-yl)[1,3]thiazolo[4,5-b]pyridin-2-yl)propanoyl]amino}propyl)pyrrolidinium tosylate, N-{3-[2-(3,4-dichlorophenyl)-1-oxidopyrrolidin-1-yl]propyl}-3-(5-morpholin-4-yl[1,3]thiazolo[4,5-b]pyridin-2-yl)propionamide, and their salts and isomers and the salts thereof.

A further group of the compounds is the compounds of general formula (IA)
where,
Q represents —N⁻—H group
and the meaning of Ar¹, R¹, R⁴, R⁵, R⁶ᵃ, R⁶ᵇ, Y, Z and Ar² is as defined above
and their salts and isomers and the salts thereof. These compounds possess increased metabolic stability.

The present invention relates furthermore to the pharmaceutical preparations containing the compounds of the general formula (I) or (IA), their isomers or salts which are preferably oral preparations, but inhalable, parenteral and transdermal preparations are also subjects of the present invention. The above pharmaceutical preparations may be solid or liquid formulations, for example tablets, pellets, capsules, patches, solutions, suspensions or emulsions. Preferred are the solid formulations, first of all the tablets and the capsules.

The above pharmaceutical preparations are made by applying the usual excipients and technological operations.

The compounds of the general formula (I) or (IA) according to the invention and their salts and isomers, and the salt thereof, can be used for the treatment of pathologies where CCR3 receptors play a role in the development of the disease.

The compounds according to the present invention can favorably used in the treatment of diseases like asthma, allergic rhinitis, atopic dermatitis, eczema, inflammatory bowel disease, ulcerative colitis, Crohn's disease, allergic conjunctivitis, multiple sclerosis, HIV-infection and diseases in conjunction with AIDS.

A further subject of the invention is the use of the compounds of the general formula (I) or (IA) according to the invention and their salts and isomers, and the salt thereof, for the treatment of the above pathologies. The suggested daily dose is 1-100 mg/person, of the active ingredient, depending on the nature and severity of the disease and the sex and weight of the patient.

A further subject of the invention is the preparation of the compounds of general formula (I) and (IA),—where the meanings of Ar¹, R¹, R⁴, R⁵, R⁶ᵃ, R⁶ᵇ, Y, Z, Ar² and Q are as defined above—and their salts and isomers, and the salt thereof.

FIG. 1. presents one of the possible methods for the preparation of the compounds of general formula (I) (process version a.)

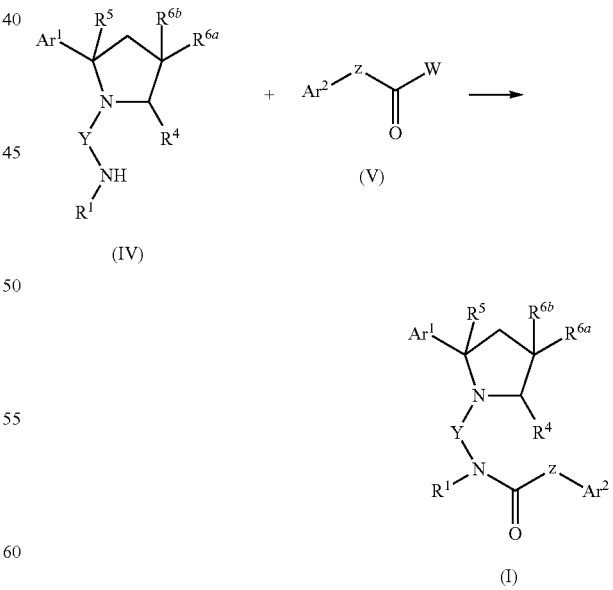

According to version a.) of the process for the preparation of the compounds of general formula (I) and their salts and isomers, and the salt thereof

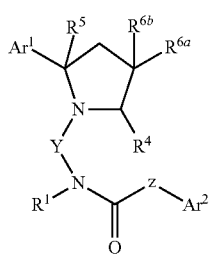

wherein the meanings of $Ar^1$, $R^1$, $R^4$, $R^5$, $R^{6a}$, $R^{6b}$, Y, Z and $Ar^2$ are as defined above—a compound of general formula (IV),

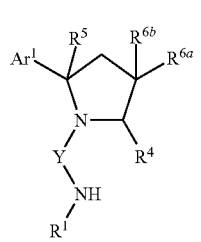

wherein the meanings of $Ar^1$, $R^1$, $R^4$, $R^5$, $R^{6a}$, $R^{6b}$ and Y, are as defined above—, is reacted with a carboxylic acid derivative of general formula (V),

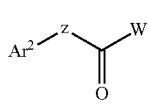

where the meanings of $Ar^2$ and Z are as defined above and W represents halogen atom, hydroxyl group, $C_{1-4}$ straight or branched alkoxy group or a —O—CO—Z—$Ar^2$ group—where the meanings of Z and $Ar^2$ are as defined above—and if desired, the substituents of the resulting compound of general formula (I) are transformed into each-other by a method known per se, and/or the resulting compound of general formula (I) is transformed into its salt, or liberated from its salt and/or separated into its optically active isomers, or the optically active isomer is transformed into the racemic compound and if desired the structural isomers are separated.

A preferred method to carry out process version a) according to the invention is to treat the acid of the general formula (V), where W represents hydroxyl group, with a reagent suitable to form acid halides, preferably thionyl chloride, to prepare the acid chloride which is then reacted with an amine of the general formula (IV) in an inert solvent (e.g. in a chlorinated hydrocarbon, such as dichloromethane, chloroform, or in ethyl acetate) in the presence of a base (e.g. triethyl amine) or in pyridine, at room temperature or at the boiling point of the solvent.

Another preferred method is when the acid of the general formula (V) is reacted with an amine of the general formula (IV) in the presence of an activating agent. Activation of the carboxylic acids may be achieved by preparation of carboxylic acid mixed anhydrides as intermediates, by use of e.g. pivalyl chloride (M. T. Leplawy: Tetrahedron 1960, 11, 39), ethyl chloroformate (T. Wieland: J. Liebigs Ann. Chem. 1951, 572, 190), isobutyl chloroformate (J. R. Vaughan: JACS. 1951, 73, 3547) or dicyclohexyl carbodiimide (DCC) (R. Arshady: J. Chem. Soc. Perkin Trans. 1, 1981, 529 or D. Hudson: J. Org. Chem. 1988, 53, 617), in an inert solvent (e.g. dichloromethane, chloroform, tetrahydrofuran, acetonitrile), in the presence of an acid-binding agent, e.g. a tertiary amine (triethylamine, N-methylmorpholine), at a temperature between −10 and 25° C.

The activation may also be achieved by use of carbonyldiimidazole (H. A. Staab: Lieb. Ann. Chem.: 1957, 609, 75), in inert solvents, preferably in dichloromethane, chloroform, tetrahydrofuran or in the mixture thereof. Activation can also be performed with benzotriazol-1-yl-oxy-tripyrrolidinophosphonium-hexafluoro-phosphate (PyBOP), in inert solvents (J. Corte: Tetrahedron Lett. 31, 1990, 205).

If the compound of the general formula (I) is a carboxylic acid ester, where in the formula W represents a $C_{1-4}$ straight or branched alkoxy group, then the reaction can be carried out favorably by the known method, at 150° C. without solvent, in melt.

The compounds of the general formula (I) according to the invention can also be prepared by the method demonstrated in FIG. 2. (process version b.).

FIG. 2.

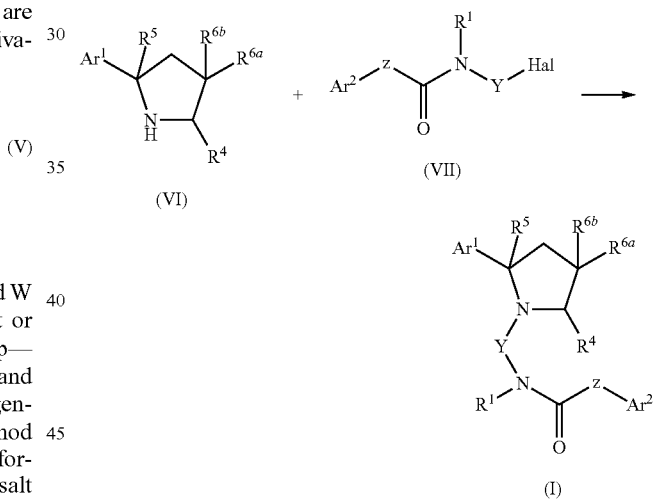

In process version b.) according to the invention the compounds of the general formula (I)—where the meanings of $Ar^1$, $R^1$, $R^4$, $R^5$, $R^{6a}$, $R^{6b}$, Y, Z and $Ar^2$ are as defined above—and their salts, isomers and the salts thereof, are prepared by reacting an amino compound of the general formula (VI),

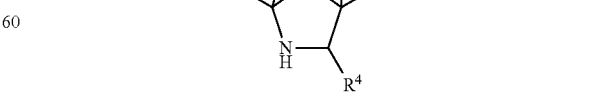

where the meanings of $Ar^1$, $R^5$, $R^4$, $R^{6a}$ and $R^{6b}$ are as defined above, with a halogen compound of the general formula (VII),

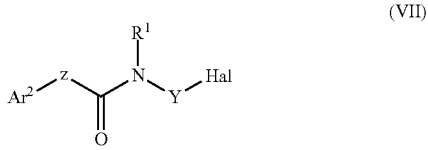

(VII)

where the meanings of Y, $R^1$, $Ar^2$ and Z are as defined above and Hal represents halogen atom—, and if desired the substituents of the resulting compound of general formula (I) are transformed into each-other by a method known per se, and/or the resulting compound of general formula (I) is transformed into its salt or liberated from its salt and/or separated into its optically active isomers, or the optically active isomer is transformed into the racemic compound and if desired the structural isomers are separated.

A preferred embodiment of process version b.) is when the reaction of the amine of the general formula (VI) and the halogen compound of the general formula (VII) is carried in an inert solvent, preferably in dichloromethane, in the presence of organic bases as acid binders.

The compounds of the general formula (IA) according to the invention—where Q represents —O⁻ group and $Ar^1$, $R^1$, $R^4$, $R^5$, $R^{6a}$, $R^{6b}$, Y, Z, $Ar^2$ have the meanings as defined above—can be prepared by the method demonstrated in FIG. 3. (process version c.).

FIG. 3.

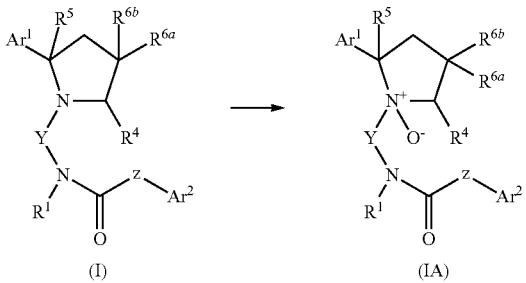

In version c.) of the process according to the invention, the compounds of the general formula (IA) and their salts and isomers and the salts thereof—where Q represents —O⁻ group

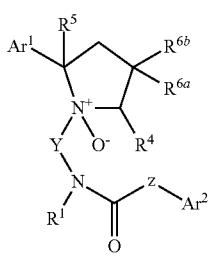

(IA)

and the meanings of $Ar^1$, $R^1$, $R^4$, $R^5$, $R^{6a}$, $R^{6b}$, Y, Z and $Ar^2$ are as defined above—are prepared so that a compound of the general formula (IA) prepared by method a.) or b),—where $Ar^1$, $R^1$, $R^4$, $R^5$, $R^{6a}$, $R^{6b}$, Y, Z and $Ar^2$ have the meanings as defined above—is oxidized and—if desired—the substituents of the compound of the general formula (IA) are transformed into each other by a method known per se, and/or the resulting compound of the general formula (IA) is transformed into its salt or liberated from its salt and/or separated into its optically active isomers, or the optically active isomer is transformed into the racemic compound and if desired the structural isomers are separated.

In version c) of the process according to the invention, the reaction is preferably carried out in an inert solvent at a temperature of 0-30° C. using known oxidants, such as hydrogen peroxide, potassium permanganate, favorably meta-chloro-perbenzoic acid. As for inert solvent halogenated solvents, such as dichloromethane, chloroform, acetonitrile, preferably dichloromethane can be used.

The compounds of the general formula (IA) according to the invention—where Q represents —N⁻—H group and $Ar^1$, $R^1$, $R^4$, $R^5$, $R^{6a}$, $R^{6b}$, Y, Z, $Ar^2$ and X have the meanings as defined above—can be prepared by the method demonstrated in FIG. 4. (process version d.).

FIG. 4.

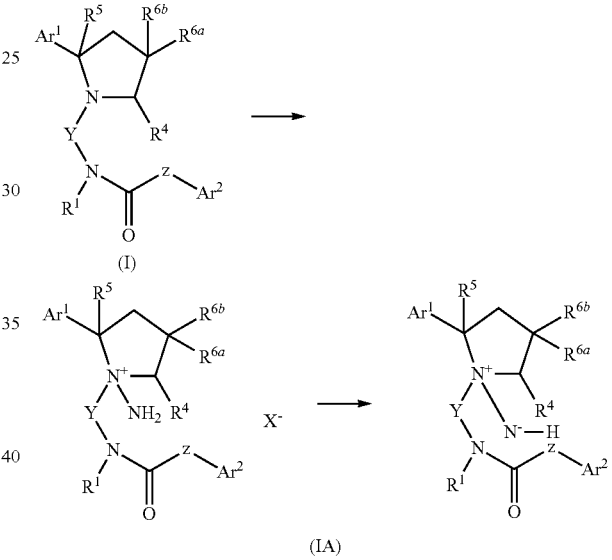

In version d.) of the process according to the invention, the compounds of the general formula (IA) and their salts and isomers and the salts thereof—where Q represents —N⁻—H group and $Ar^1$, $R^1$, $R^4$, $R^5$, $R^{6a}$, $R^{6b}$, Y, Z, $Ar^2$ and X have the meanings as defined above—can be prepared so that a compound of the general formula (IA) prepared by method a.) or b.)—where $Ar^1$, $R^1$, $R^4$, $R^5$, $R^{6a}$, $R^{6b}$, Y, Z and $Ar^2$ have the meanings as defined above—is reacted with O-tosylhydroxylamine to obtain the tosylate salt, which after alkaline treatment results the zwitterionic structure, and—if desired—the substituents of the resulting compound of the general formula (IA) are transformed into each other by a method known per se, and/or the resulting compound of the general formula (IA) is transformed into its salt or liberated from its salt and/or separated into its optically active isomers, or the optically active isomer is transformed into the racemic compound and if desired the structural isomers are separated.

The reaction is preferably carried out in an inert solvent at a temperature of 0-50° C. using O-tosylhydroxylamine. As for inert solvent, halogenated solvents, such as dichloromethane, chloroform, tetrahydrofuran, acetonitrile, preferably dichloromethane can be used.

The compounds of the general formula (IA) according to the invention—where Q represents —N⁻—CO—R¹⁰ group and Ar¹, R¹, R⁴, R⁵, R⁶ᵃ, R⁶ᵃ, R⁶ᵇ, Y, Z, R¹⁰ and Ar² have the meanings as defined above—can be prepared by the method demonstrated in FIG. 5. (process version e.).

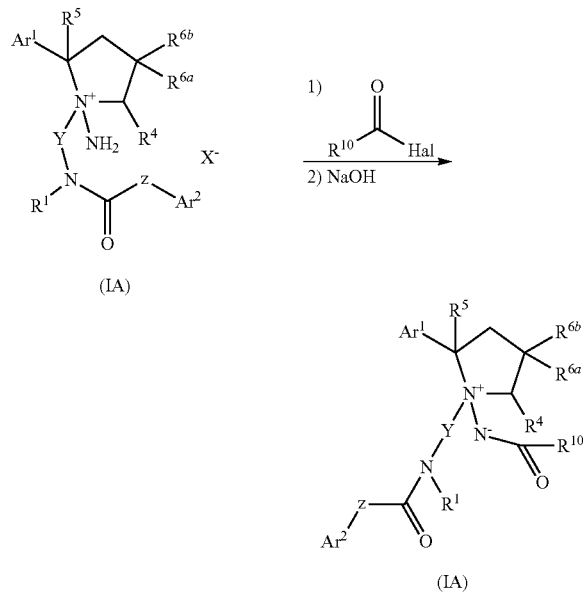

FIG. 5.

In version e.) of the process according to the invention, the compounds of the general formula (IA) and their salts and isomers and the salts thereof—where Q represents —N⁻— CO— group, wherein R¹⁰ stands for hydrogen atom, $C_{1-4}$ straight or branched alkyl group, $C_{3-6}$ cycloalkyl, phenyl or benzyl group, and Ar¹, R¹, R⁴, R⁵, R⁶ᵃ, R⁶ᵇ, Y, Z and Ar² have the meanings as defined above—can be prepared so that a compound of the general formula (IA) prepared by method d.)—where Ar¹, R¹, R⁴, R⁵, R⁶ᵃ, R⁶ᵇ, Y, Z and Ar² have the meanings as defined above—is acylated with a compound of the general formula Hal-CO—R¹⁰—where R¹⁰ has the meaning as defined above and Hal represents halogen atom, and— if desired—the substituents of the resulting compound of the general formula (IA) are transformed into each other by a method known per se, and/or the resulting compound of the general formula (IA) is transformed into its salt or liberated from its salt and/or separated into its optically active isomers, or the optically active isomer is transformed into the racemic compound, and—if desired—the structural isomers are separated. The acylation is preferably performed with alkyl or aralkyl acid halides, in inert solvents, preferably in dichloromethane, using organic or inorganic acid binders, preferably potassium carbonate.

In version f.) of the process according to the invention, the compounds of the general formula (IA) and their salts and isomers and the salts thereof—where Q represents —N⁻— CO—R¹⁰ group, wherein R¹⁰ stands for —NH—R¹¹ group and Ar¹, R¹, R⁴, R⁵, R⁶ᵃ, R⁶ᵇ, Y, Z, Ar² and R¹¹ have the meanings as defined above—can be prepared so that a compound of the general formula (IA) prepared by method d.)— where Q represents —N⁻—H group and Ar¹, R¹, R⁴, R⁵, R⁶ᵃ, R⁶ᵇ, Y, Z and Ar² have the meanings as defined above—is reacted with a compound of the general formula R¹¹NCO where R¹¹ has the meaning as defined above, and—if desired—the substituents of the resulting compound of the general formula (IA) are transformed into each other by a method known per se, and/or the resulting compound of the general formula (IA) is transformed into its salt or liberated from its salt and/or separated into its optically active isomers, or the optically active isomer is transformed into the racemic compound, and—if desired—the structural isomers are separated. The urea is preferably formed by use of alkyl or aralkyl isocyanates in inert solvents, preferably in dichloromethane or dioxane, favorably in the presence of potassium carbonate.

Separation of the enantiomers of the racemic compounds of general formula (I) or (IA) can be performed by chiral preparative column chromatography or by any other method known for the resolution of compounds of basic character.

The compounds of the general formula (IV)—where the meanings of Ar¹, R¹, R⁴, R⁵, R⁶ᵃ, R⁶ᵇ and Y, are as defined above—can be most generally prepared by alkylating the amine derivatives of the general formula (VI) with the commercially available halogeno-alkylamines of the general formula (XVII), preferably with bromo-alkylamines, or with the salts thereof (FIG. 6.), in alcoholic media, preferably in boiling i-propanol, often in the presence of an acid binding base, such as triethylamine or DBU.

FIG. 6.

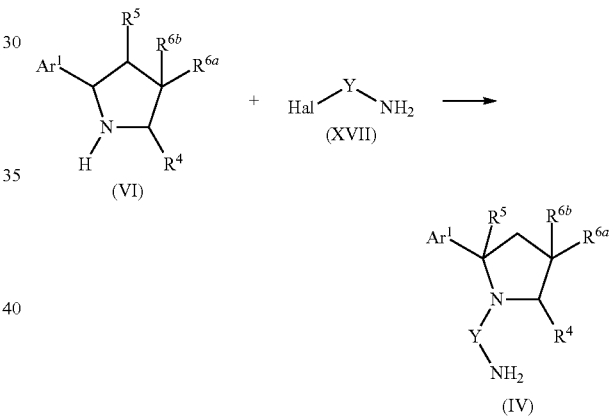

For the preparation of a diamine of the general formula (IV) from the compound of the general formula (VI), an additional route is also available. If Y stands for straight $C_{3-4}$ alkylene group, optionally substituted by one or more, identical or non-identical $C_{1-4}$ straight or branched alkyl group, the alkylation reaction can be carried out using halogen-alkyl-cyanides of the general formula (XVIII),—some of which can be purchased, others can be prepared by methods known in the literature—, preferably in dimethylformamide, in the presence of an acid binding base, preferably triethylamine, at a temperature between 20° C. and reflux temperature. In the nitrile of the general formula (XIV), R¹³ and R¹⁴ independently represent hydrogen atom or $C_{1-4}$ straight or branched alkyl group and the value of r equals 0 or 1. The diamines of the general formula (IV) can be obtained from compounds (XIV) by catalytic hydrogenation by analogy of methods known in the literature, in alcoholic or hexane solution, in the presence of ammonia, using Raney nickel or rhodium catalyst, in a given case under pressure (Shapiro et al.: JACS 1959, 81, 3084 and Roufos: J. Med. Chem. 1996, 39, 7, 1514). (FIG. 7.).

FIG. 7.

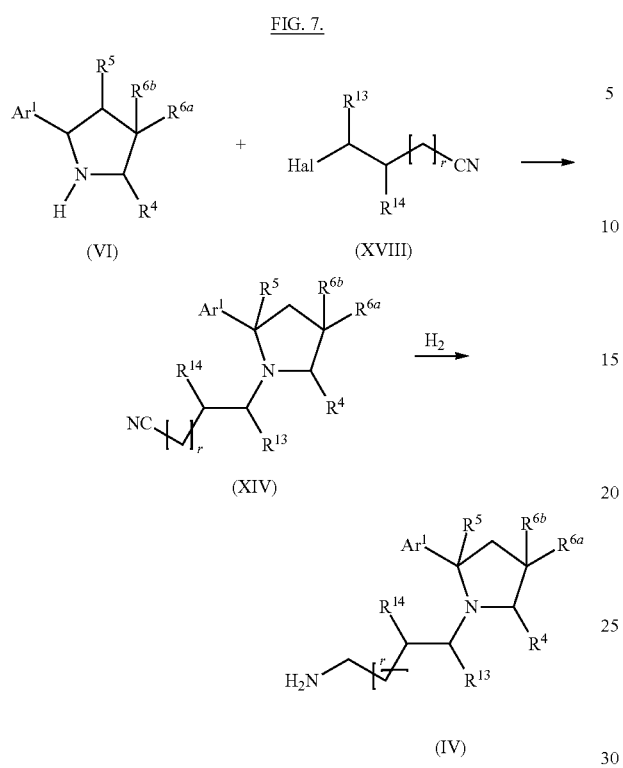

If Y stands for 1,3-propylene, 1-methyl-1,3-propylene, 2-methyl-1,3-propylene or 1,4-butylene ($R^{15}$ and $R^{16}$ independently represent hydrogen atom or methyl group, r equals 0 or 1), and the meanings of the other substituents are as defined above, the cyanides of the general formula (XIV) can be prepared from the amines of the general formula (VI) with the alkene-cyanides of the general formula (XIII) by literature analogy (FIG. 8.) (King et al.: JACS. 1946, 68, 1468). The alkene-cyanides of the general formula (XIII) are commercially available. The diamines of the general formula (IV) can be obtained from the compounds of the general formula (XIV) by catalytic hydrogenation as described above.

FIG. 8.

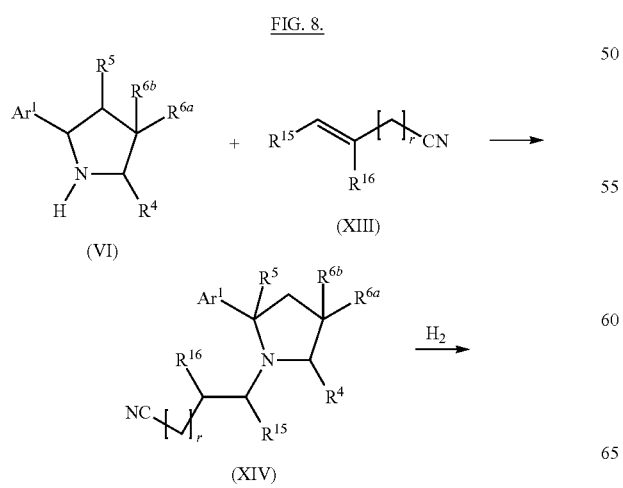

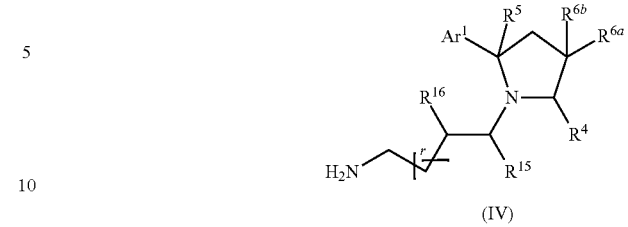

The diamines of the general formula (IV) where Y stands for 3-methylpropylene, and the meanings of the other substituents are as defined above, can also be prepared by the method demonstrated in FIG. 9. Mannich reaction performed from the amines of the general formula (VI) with paraformaldehyde and acetone results the compound of the general formula (XV). The reaction, after literature analogy, can be carried out in i-propanol at reflux temperature (JACS. 1959, 81, 2214-18). The oximes of the general formula (XVI) can be prepared from the compound of the general formula (XV) with hydroxylamine, in aqueous i-propanol solution, after analogous examples taken from the literature (JACS. 1959, 81, 2214-18). The amine of the general formula (IV) can be obtained from the oxime of the general formula (XVI) by literature analogy, by catalytic hydrogenation in the presence of Raney-nickel catalyst, in ethanol-ammonia.

FIG. 9.

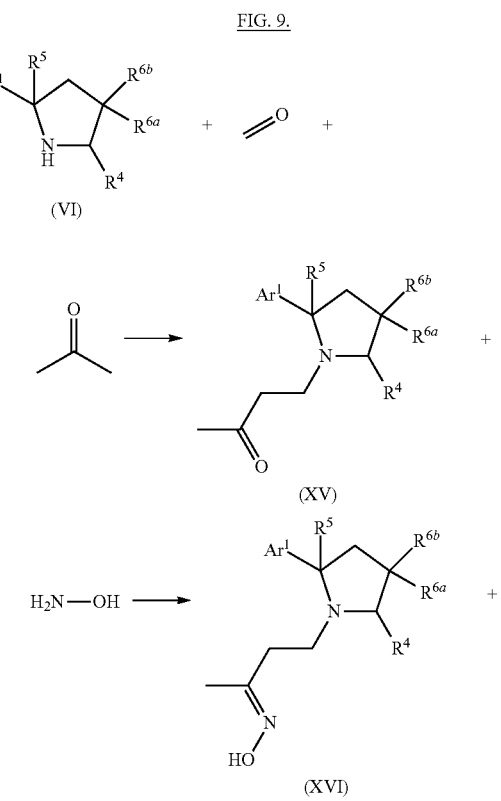

-continued

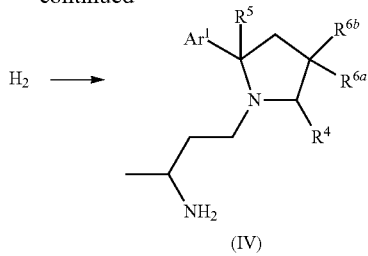

(IV)

The pyrrolidine derivatives where in the formula $R^5$, $R^4$, $R^{6a}$, $R^{6b}$ represent hydrogen atom, can be prepared by the method known in the literature (J. Org. Chem. 23, 1958, 1281 and J. Med. Chem. 1972, 15, 827), demonstrated in FIG. 10. Reacting substituted bromobenzenes with 4-chlorobutyronitrile in Grignard reaction in the presence of magnesium, the derivative (IX) can be obtained which is hydrogenated using Pt—C catalyst.

FIG. 10.

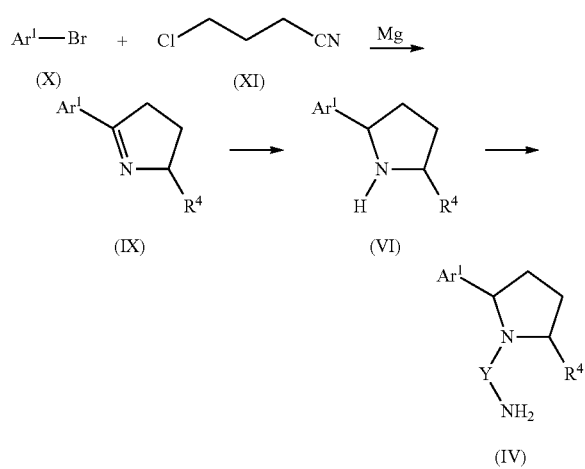

In another route, from the substituted 4-oxo-4-phenylbutyronitrile (XII) the 5-phenyl-3,4-dihydro-2H-pyrrol (IX) is obtained which after hydrogenation in the presence of Raney-nickel results the derivative (VI) (J. Org. Chem. 23, 1958, 1281), FIG. 11.

FIG. 11.

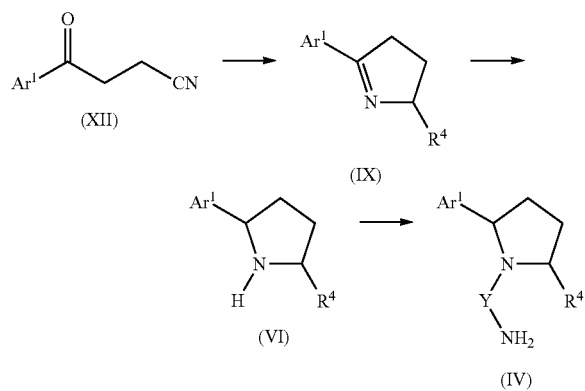

If $R^5=C_{1-4}$ straight or branched alkyl group, $R^4=R^{6a}=R^{6b}=H$, the preparation of compound (VI) can be carried out by analogy of literature reference (Tetrahedron Lett. 34, 39, 1993, 6205).

If $R^{6a}=R^{6b}=R^5=H$ and $R^4=C_{1-4}$ straight or branched alkyl group, the preparation of compound (VI) can be carried out by literature analogy (Monatsh. Chem., 83, 1952, 523).

If $R^{6a}$ or $R^{6b}$ represent $C_{1-4}$ straight or branched alkyl group and the other substituents are hydrogen atoms, the compound can be prepared by literature analogy (Chem. Ber. 125, 10, 1992, 2243-48).

If $R^{6a}=R^{6b}$ represent $C_{1-4}$ straight or branched alkyl group and the other substituents are hydrogen atoms, the compound can be prepared by literature analogy (J. Org. Chem. 32, 1967, 3241).

The compounds of the general formulae (X), (XI) and (XII) are described in the literature.

The compounds of the general formulae (V) and (VII)—wherein $Ar^2$, Z, $R^1$, Y, W, Z and Hal have the meanings as defined above—can be prepared as described in patent application of publication number WO 2007/034252, or in analogous manner.

EXAMPLES

Example 1

N-{3-[2-(3,4-Dichlorophenyl)pyrrolidin-1-yl]propyl}-3-(5-methoxy[1,3]thiazolo[5,4-b]pyridin-2-yl)propionamide In the general formula (I) $Ar^1$ represents 3,4-dichlorophenyl group, $R^4$, $R^5$, $R^{6a}$, $R^{6b}$, $R^1$ represent hydrogen atom, Y represents 1,3-propylene group, Z represents 1,2-ethylene group, $Ar^2$ stands for 5-methoxy[1,3]thiazolo[5,4-b]pyridin-2-yl group.

a.) 5-(3,4-Dichlorophenyl)-3,4-dihydro-2H-pyrrole

Related literature for the preparation of the compound: J. Med. Chem. 15, 1972, 827 b.) 2-(3,4-Dichlorophenyl)pyrrolidine

Related literature for the preparation of the compound: J. Med. Chem. 15, 1972, 827 c.) 3-[2-(3,4-Dichlorophenyl)pyrrolidin-1-yl]-propan-1-nitrile

To the solution of 2.4 g (11.2 mmol) 2-(3,4-dichlorophenyl)pyrrolidine in 13 ml abs. methanol dropwise under stirring at room temperature 2.21 ml (33.6 mmol) acrylonitrile is added. The reaction mixture is stirred for 3 days at room temperature, then evaporated. The residue is purified by column chromatography using at first chloroform, then chloroform:methanol 100:1 ratio mixture as eluent, to obtain 2.1 g title compound in the form of an oil. LC-MS[MH$^+$]=269 ($C_{13}H_{14}Cl_2N_2$ 269.14).

d.) 3-[2-(3,4-Dichlorophenyl)pyrrolidin-1-yl]propane-1-amine 1.9 g (7.1 mmol) nitrile is dissolved in 143 ml methanol-ammonium hydroxide 4:1 mixture and hydrogenated in a H-CUBE THALES apparatus under 30 bar pressure at 45° C.

The reaction mixture is evaporated to obtain 3.1 g title compound in the form of an oil. LC-MS[MH$^+$]=273 (C$_{13}$H$_{18}$Cl$_2$N$_2$ 273.205)

e.) N-{3-[2-(3,4-Dichlorophenyl)pyrrolidin-1-yl]propyl}-3-(5-methoxy[1,3]thiazolo[5,4-b]pyridin-2-yl)propionamide To the solution of 0.33 g (1.4 mmol) 6-methoxy-[1,3]thiazolo[5,4-b]pyridin-2-yl-propionic acid in 9 ml abs. dimethylformamide 0.34 g (2.8 mmol) carbonyl-diimidazole is added. The mixture is stirred at room temperature for 0.5 h. then the solution of 0.38 g (1.4 mmol) 3-[2-(3,4-dichlorophenyl)pyrrolidin-1-yl]propane-1-amine in 8.5 ml abs. dimethylformamide, as obtained in point d.) but also containing 0.48 ml (0.35 g, 3.5 mmol) triethylamine, is added to it. The reaction mixture is stirred at room temperature overnight and evaporated in vacuum. The residue is mixed with crushed ice, extracted with 3×15 ml ether, dried over sodium sulfate and evaporated in vacuum. After purification by column chromatography using chloroform-methanol 100:1 mixture as eluent, 0.3 g title compound is obtained in the form of an oil.

LC-MS[MH$^+$]=493 (C$_{23}$H$_{26}$Cl$_2$N$_2$O$_2$S 493.456)

$^1$H NMR: 7.51, d, 1.9 Hz (1H), 6.95, d, 8.1 Hz (1H), 7.28, dd, 8.1 & 1.9 Hz (1H), 3.19, m (1H), 1.45, m (1H), 2.10, m (1H), 1.65-1.85 (2H), 2.09, m (1H) 3.19, m (1H), 2.00, m (1H), 2.37, m (1H), 1.40-1.55, m (2H), 2.90-3.10, m (2H), 7.84, t, 5.3 Hz (N—H), 2.56, t, 7.2 Hz (2H), 3.24, t, 7.2 Hz (2H), 8.17, d, 8.4 Hz (1H), 6.95, d, 8.4 Hz (1H), 3.92, s (3H)

According to the process described in Example 1. the following compounds of Table 1. are prepared:

TABLE 1

| Example | Ar$^2$ | [MH$^+$] | Rt (min) | Mp (° C.) |
|---|---|---|---|---|
| 2. | 2-methyl-5-(methylamino)thiazolo[5,4-b]pyridine | 492 | 4.74 | 119-121 |
| 3. | 2-methyl-5-(pyrrolidin-1-yl)thiazolo[5,4-b]pyridine | 532 | 6.37 | 137-138 |
| 4. | 2-methyl-5-(piperidin-1-yl)thiazolo[5,4-b]pyridine | 546 | 7.41 | 93-95 |
| 5. | 2-methyl-5-(morpholin-4-yl)thiazolo[5,4-b]pyridine | 548 | 5.76 | 111-112 |
| 6. | 2,6-dimethylthiazolo[5,4-b]pyridine | 477 | 5.32 | 125-130 |
| 7. | 2-methyl-5-(4-methylpiperazin-1-yl)thiazolo[5,4-b]pyridine | 561 | 4.74 | |
| 8. | 2,6-dimethylbenzothiazole | 476 | 6.82 | 76-79 |
| 9. | 2-methyl-6-(piperidin-1-yl)thiazolo[5,4-b]pyrazine | 547 | 6.74 | 105 |
| 10. | 2-methyl-6-(morpholin-4-yl)thiazolo[5,4-b]pyrazine | 549 | 5.34 | 165 |
| 11. | 2-methyl-5-(2,6-dimethylmorpholin-4-yl)thiazolo[5,4-b]pyridine | 576 | 6.60 | |

Chemical name of the compounds mentioned in Table 1:

2. N-{3-[2-(3,4-dichlorophenyl)pyrrolidin-1-yl]propyl}-3-(5-(methylamino)[1,3]thiazolo[5,4-b]pyridin-2-yl)propionamide 3. N-{3-[2-(3,4-dichlorophenyl)pyrrolidin-1-yl]propyl}-3-(5-pyrrolidin-1-yl[1,3]thiazolo[5,4-b]pyridin-2-yl)propionamide 4. N-{3-[2-(3,4-dichlorophenyl)pyrrolidin-1-yl]propyl}-3-(5-piperidin-1-yl[1,3]thiazolo[5,4-b]pyridin-2-yl)propionamide
5. N-{3-[2-(3,4-dichlorophenyl)pyrrolidin-1-yl]propyl}-3-(5-morpholin-4-yl[1,3]thiazolo[5,4-b]pyridin-2-yl)propionamide,
6. N-{3-[2-(3,4-dichlorophenyl)pyrrolidin-1-yl]propyl}-3-(5-methyl[1,3]thiazolo[5,4-b]pyridin-2-yl)propionamide,
7. N-{3-[2-(3,4-dichlorophenyl)pyrrolidin-1-yl]propyl}-3-(5-(4-methylpiperazin-1-yl)[1,3]thiazolo[5,4-b]pyridin-2-yl)propionamide,
8. N-{3-[2-(3,4-dichlorophenyl)pyrrolidin-1-yl]propyl}-3-(6-methyl-1,3-benzothiazol-2-yl)propionamide,
9. N-{3-[2-(3,4-dichlorophenyl)pyrrolidin-1-yl]propyl}-3-(6-piperidin-1-yl)[1,3]thiazolo[4,5-b]pyrazin-2-yl)propionamide,
10. N-{3-[2-(3,4-dichlorophenyl)pyrrolidin-1-yl]propyl}-3-(6-morpholin-4-yl)[1,3]thiazolo[4,5-b]pyrazin-2-yl)propionamide,
11. N-{3-[2-(3,4-dichlorophenyl)pyrrolidin-1-yl]propyl}-3-(5-(2,6-dimethylmorpholin-4-yl)[1,3]thiazolo[5,4-b]pyridin-2-yl)propionamide.

Example 12

N-(3-[2-(3,4-Dichlorophenyl)pyrrolidin-1-yl]-1-methylpropyl)-3-(5-morpholin-4-yl[1,3]thiazolo[5,4-b]pyridin-2-yl)]propionamide In the general formula (I) $Ar^1$ represents 3,4-dichlorophenyl group, $R^4$, $R^5$, $R^{6a}$, $R^{6b}$, $R^1$ represent hydrogen atom, Y represents —$CH_2$—$CH_2$—$CH(CH_3)$— group, Z represents 1,2-ethylene group, $Ar^2$ stands for 5-morpholin-4-yl[1,3]thiazolo[5,4-b]pyridin-2-yl group.

a.) 4-[2-(3,4-Dichlorophenyl)pyrrolidin-1-yl]butan-2-one

To the solution of 4 g (18.5 mmol) 2-(3,4-dichlorophenyl)-pyrrolidine in 10 ml acetone, during ice-water cooling, the mixture of 10 ml acetone and 1.6 ml cc. hydrochloric acid is added. The mixture is stirred for 15 minutes under cooling for 10 minutes at room temperature, then the solution of 0.83 g (9.3 mmol) paraformaldehyde in 9.2 ml iso-propanol is added and the reaction mixture is heated at reflux temperature for 4 hours. After cooling, 15 ml of water is added and the mixture is extracted with 3×20 ml dichloromethane, dried over sodium sulfate and evaporated in vacuum. The residue is crystallized in hexane to obtain 2.11 g title compound. Mp: 160-162° C.

b.) (2E)-4-[2-(3,4-Dichlorophenyl)pyrrolidin-1-yl]butan-2-one oxime 2.11 g (7.4 mmol) of 4-[2-(3,4-dichlorophenyl)pyrrolidin-1-yl]butan-2-one as obtained in point a.) is suspended in 11.7 ml iso-propanol and the solution of 0.54 g (7.7 mmol) hydroxylamine hydrochloride in 5 ml of water is added to it. The mixture is stirred for 2 hours. The alcohol is distilled off, the aqueous residue is made alkaline with 5N sodium hydroxide solution, from the resulting sticky precipitate the water is decanted, the residue treated with ether, filtered off and washed with ether. 1.13 g title compound is obtained. Mp: 145-147° C.

c.) 4-[2-(3,4-Dichlorophenyl)pyrrolidin-1-yl]butan-2-amine 0.9 g (2.99 mmol) 4-[2-(3,4-dichlorophenyl)pyrrolidin-1-yl]butan-2-one oxime as obtained in section b.) is hydrogenated in 100 ml methanol in the presence of Raney-nickel catalyst. After evaporation of the solvent 0.68 g title compound is obtained in the form of an oil. LC-MS[MH$^+$]=287 ($C_{14}H_{20}Cl_2N_2$ 287.23).

d.) N-(3-[2-(3,4-Dichlorophenyl)pyrrolidin-1-yl]-1-methylpropyl)-3-(5-morpholin-4-yl[1,3]thiazolo[5,4-b]pyridin-2-yl)]propionamide 0.2 g (0.68 mmol) 5-morpholin-4-yl[1,3]thiazolo[5,4-b]pyridine is dissolved in 5 ml abs. dimethylformamide and 0.106 g (0.65 mmol) carbonyl-diimidazole is added. The mixture is stirred at room temperature for 1 hour, then the solution of 0.15 g (0.55 mmol) 4-[2-(3,4-dichlorophenyl)pyrrolidin-1-yl]butan-2-amine in 4 ml abs. dimethylformamide, as obtained in section d.) but also containing 0.19 ml (1.36 mmol) triethylamine, is added to it. The reaction mixture is stirred at room temperature overnight then poured onto ice-water, extracted with 4×10 ml ether, dried over sodium sulfate, evaporated and purified by column chromatography using chloroform-methanol 9:1 mixture as eluent. The resulting oil is treated with hexane to obtain 85 mg title compound. Mp: 128-132° C., LC-MS[MH$^+$]=562, Rt=6.04 min.

Example 13

N-(3-[2-(3,4-Dichlorophenyl)pyrrolidin-1-yl]-1-methylpropyl)-3-(5-piperidin-1-yl[1,3]thiazolo[5,4-b]pyridin-2-yl)]propionamide In the general formula (I) $Ar^1$ represents 3,4-dichlorophenyl group, $R^4$, $R^5$, $R^{6a}$, $R^{6b}$, $R^1$ represent hydrogen atom, Y represents —$CH_2$—$CH_2$—$CH(CH_3)$— group, Z represents 1,2-ethylene group, $Ar^2$ stands for 5-piperidin-1-yl[1,3]thiazolo[5,4-b]pyridin-2-yl group.

As described in Example 12. but starting from 0.287 g (1 mmol) of 4-[2-(3,4-dichlorophenyl)pyrrolidin-1-yl]butan-2-amine and 0.29 g (1.02 mmol) 5-piperidin-1-yl[1,3]thiazolo[5,4-b]pyridine, 0.21 g crystalline title compound is obtained. Mp: 134-140° C., LC-MS[MH$^+$]=560, Rt=7.71 min.

Example 14

1-Amino-2-(3,4-dichlorophenyl)-1-(3-{[3-(5-pyrrolidin-1-yl[1,3]thiazolo[4,5-b]pyridin-2-yl)propanoyl]amino}propyl)pyrrolidinium tosylate In the general formula (IA) $Ar^1$ represents 3,4-dichlorophenyl group, $R^4$, $R^5$, $R^{6a}$, $R^{6b}$, $R^1$ represent hydrogen atom, Y represents 1,3-propylene group, Z represents 1,2-ethylene group, $Ar^2$ stands for 5-pyrrolidin-1-yl[1,3]thiazolo[5,4-b]pyridin-2-yl group, Q stands for —N$^-$—H group.

To the solution of 0.34 g (0.64 mmol) N-{3-[2-(3,4-dichlorophenyl)pyrrolidin-1-yl]propyl}-3-(5-pyrrolidin-1-yl[1,3]thiazolo[5,4-b]pyridin-2-yl)propionamide in 10 ml dichloromethane and 6 ml dimethylformamide, 0.26 g (1.92 mmol) potassium carbonate and then dropwise, under ice-water cooling, the solution of 0.18 g (0.96 mmol) O-tosylhydroxylamine in 10 ml dichloromethane are added. The reaction mixture is stirred under ice-water cooling for 2 hours, then 20 ml of water is added, the phases are separated, the organic phase is washed with 20 ml of water, dried over sodium sulfate and evaporated. The residual oil is crystallized with ether to obtain 0.34 g title compound. Mp: 115-118° C., LC-MS[M$^+$]=547, Rt=4.37 min.

According to the process described in Example 14. the following compounds of Table 2. are prepared:

TABLE 2

Chemical name of the compounds mentioned in Table 2:

| Example | Ar² | Mp (° C.) | Rt (min) | [M⁺] |
|---|---|---|---|---|
| 15. | 2-methyl-5-(piperidin-1-yl)[1,3]thiazolo[4,5-b]pyridin-2-yl | 119-122 | 4.97 | 561 |
| 16. | 2-methyl-5-(morpholin-4-yl)[1,3]thiazolo[4,5-b]pyridin-2-yl | 215-218 | 3.89 | 563 |
| 17. | 2,5-dimethyl[1,3]thiazolo[4,5-b]pyridin-2-yl | 103-106 | 3.51/3.58 | 492 |
| 18. | 2-methyl-5-(2,6-dimethylmorpholin-4-yl)[1,3]thiazolo[4,5-b]pyridin-2-yl | 102-106 | 4.08 | 591 |

Chemical name of the compounds mentioned in Table 2:
15. 1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate,
16. 1-amino-2-(3,4-dichlorophenyl)-1-(3-{[3-(5-morpholin-4-yl[1,3]thiazolo[4,5-b]pyridin-2-yl)propanoyl]amino}propyl)pyrrolidinium tosylate,
17. 1-amino-2-(3,4-dichlorophenyl)-1-(3-{[3-(5-methyl[1,3]thiazolo[4,5-b]pyridin-2-yl)propanoyl]amino}propyl)pyrrolidinium tosylate,
18. 1-amino-2-(3,4-dichlorophenyl)-1-[3-({3-(5-(2,6-dimethylmorpholin-4-yl)[1,3]thiazolo[4,5-b]pyridin-2-yl)propanoyl]amino}propyl)pyrrolidinium tosylate.

Example 19

N-{3-[2-(3,4-Dichlorophenyl)-1-oxidopyrrolidin-1-yl]propyl}[3-(5-methyl-1,3-benzothiazol-2-yl)propionamide In the general formula (IA) Ar¹ represents 3,4-dichlorophenyl group, $R^4$, $R^5$, $R^{6a}$, $R^{6b}$, $R^1$ represent hydrogen atom, Y represents 1,3-propylene group, Z represents 1,2-ethylene group, Ar² stands for 5-methyl-benzthiazol-2-yl group and Q represents —O⁻ group.

The solution of 0.146 g (0.31 mmol) N-{3-[2-(3,4-dichlorophenyl)pyrrolidin-1-yl]propyl}-3-(5-methyl-1,3-benzthiazol-2-yl)propionamide in 5 ml dichloromethane is cooled to 0° C., 53 mg (0.31 mmol) m-chloroperbenzoic acid is added to it under stirring and the mixture is stirred for 1 hour. The acid is neutralized with solid potassium carbonate, the precipitated salts are filtered off, the dichloromethane solution is evaporated. The residue is purified by column chromatography using chloroform-methanol 9:1 mixture as eluent to obtain 88 mg title compound in the form of white crystals. Mp. 145-148° C., [MH⁺]=492, Rt=4.31 min.

According to the process described in Example 19. the following compounds of Table 3. are prepared:

TABLE 3

| Example | Ar² | Mp (° C.) | [MH⁺] | Rt (min) |
|---|---|---|---|---|
| 20. | 2-methyl-5-(piperidin-1-yl)[1,3]thiazolo[4,5-b]pyridin-2-yl | 185-187 | 562 | 2.91 |
| 21. | 2-methyl-5-(morpholin-4-yl)[1,3]thiazolo[4,5-b]pyridin-2-yl | 172-175 | 564 | 3.72 |
| 22. | 2-methyl-5-(pyrrolidin-1-yl)[1,3]thiazolo[4,5-b]pyridin-2-yl | 185-188 | 548 | 4.19 |

Chemical name of the compounds mentioned in Table 3:
20. N-{3-[2-(3,4-dichlorophenyl)-1-oxidopyrrolidin-1-yl]propyl}-3-(5-piperidin-1-yl)[1,3]thiazolo[4,5-b]pyridin-2-yl)propionamide,
21. N-{3-[2-(3,4-dichlorophenyl)-1-oxidopyrrolidin-1-yl]propyl}-3-(5-morpholin-4-yl[1,3]thiazolo[4,5-b]pyridin-2-yl)propionamide,
22. N-{3-[2-(3,4-dichlorophenyl)-1-oxidopyrrolidin-1-yl]propyl}-3-(5-pyrrolidin-1-yl[1,3]thiazolo[4,5-b]pyridin-2-yl)propionamide.

Example 23

1-(Acetylamino)-2-(3,4-dichlorophenyl)-1-(3-{[3-(5-piperidin-1-yl[1,3]thiazolo[4,5-b]pyridin-2-yl)propanoyl]amino}propyl)pyrrolidinium hydrochloride In the general formula (IA) Ar¹ represents 3,4-dichlorophenyl group, $R^4$, $R^5$, $R^{6a}$, $R^{6b}$, $R^1$ represent hydrogen atom, Y represents 1,3-propylene group, Z represents 1,2-ethylene group, Ar² stands for 5-piperidin-1-yl[1,3]thiazolo[5,4-b]pyridin-2-yl group, Q represents —N⁻—CO—CH₃ group.

To the solution made of 0.11 g (0.15 mmol) 1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate and 25 ml dichloromethane, 0.083 g (0.6 mmol) potassium carbonate and 0.013 ml (0.18 mmol) acetyl chloride are added and the mixture is refluxed for 6 hours. Then, additional 0.166 g (1.2 mmol) potassium carbonate and 0.026 ml (0.36 mmol) acetyl chloride are added and the mixture is refluxed for 16 hours. The addition of potassium carbonate and acetyl chloride is repeated twice and the mixture is refluxed for further 50 hours. The reaction mixture is filtered, the precipitated inorganic salts are washed with dichloromethane, the organic phase is evaporated and purified by flash chromatography using dichloromethane-methanol 95:5 mixture. The united fractions are dissolved in 10 ml water, made alkaline with 1N sodium hydroxide, extracted with 3×5 ml dichloromethane, dried over sodium sulfate and evaporated. From the oily residue the salt is formed with hydrogen chloride in ether solution to obtain 0.8 g title compound in the form of crystals. Mp: 77-80° C., [M$^+$]=603, Rt=4.62/4.71/5.13 min.

Example 24

1-(3-Ethyl-ureido)-2-(3,4-dichlorophenyl)-1-(3-{[3-(5-(2,6-dimethyl-morpholin-4-yl)[1,3]thiazolo[4,5-b]pyridin-2-yl)propanoyl]amino}propyl)pyrrolidinium hydrochloride In the general formula (IA) Ar$^1$ represents 3,4-dichlorophenyl group, R$^4$, R$^5$, R$^{6a}$, R$^{6b}$, R$^1$ represent hydrogen atom, Y represents 1,3-propylene group, Z represents 1,2-ethylene group, Ar$^2$ stands for 2,6-dimethyl-morpholin-4-yl[1,3]thiazolo[5,4-b]pyridin-2-yl group, Q represents —N$^-$—CO—NH—C$_2$H$_5$ group—

To the solution made of 0.13 g (0.17 mmol) 1-amino-2-(3,4-dichlorophenyl)-1-(3-{[3-(2,6-dimethylmorfolin-4-yl[1,3]thiazolo[4,5-b]pyridin-2-yl)propanoyl]amino}propyl)pyrrolidinium tosylate and 15 ml dichloroethane, 0.1 g (0.51 mmol) potassium carbonate and 0.05 ml (0.63 mmol) ethyl isocyanate are added and the mixture is refluxed for 10 hours. After cooling, the organic part is evaporated. The residue is taken up in 10 ml water and extracted with 3×10 ml dichloroethane. The united organic phase is dried, filtered, evaporated in vacuum and purified by flash chromatography using dichloromethane-methanol 98:5 mixture. From the oily residue the salt is formed in dichloromethane with hydrogen chloride in ether solution to obtain 0.1 g title compound in the form of crystals. Mp: 115-118° C., [M$^+$]=662, Rt=5.52 min.

Example 25

By known methods tablets of the following composition are prepared:

| | |
|---|---|
| Active ingredient: | 40 mg |
| Lactose: | 35 mg |
| Avicel: | 21 mg |
| Crospovidone: | 3 mg |
| Magnesium stearate: | 1 mg |

Example 26

A.) Human Recombinant CCR3 Receptor (hr-CCR3) Binding Assay

The CCR3 receptor antagonist effect of the compounds of general formula (I) was examined on eotaxin binding test on hCCR3 receptor expressing recombinant K562 and RBL2H3 cells. To the tests Eotaxin labelled with radioactive iodine $^{125}$I-(2200 Ci/mmol) was used.

In the assay 200.000 cells are incubated in the presence of 0.11 nM $^{125}$I-Eotaxin, incubation: 60 minutes at 37° C. Composition of the assay buffer: RPMI-1640 medium, pH=7.6 (GIBCO), [containing 80 mg CHAPS, 500 BSA (protease free), 100 mg gelatin, 3 ml 25 mM HEPES in 100 ml RPMI]. The test compounds are dissolved in DMSO, the stock solution is diluted with the assay buffer. The final DMSO concentration is not more than 1%. The cells are incubated with the test compounds for 15 minutes, then the labelled eotaxin is added. The non-specific binding is determined in the presence of 200 nM non-labelled eotaxin. After 1 hour of incubation, 500 µl ice-cold assay buffer containing 0.5 M NaCl solution is added. Since the experiments were performed in deep-well plates, the reaction is terminated by centrifugation in plate centrifuge (JUAN) at 3600 g for 6 minutes. The supernatants are poured off by turning the plates in upside-down position. The remaining droplets were blotted with tissue paper.

For solubilization 200 µl 0.5 M NaOH solution is added to the pellets. After 1 hour of solubilization at room temperature the radioactivity is counted in gamma counter (1470 Wizard, Wallac).

The radioactivity of the solution is in direct ratio with the number of the receptors of the cells, with the amount of the bound $^{125}$I-Eotaxin and with the activity of the tested antagonist.

The specific binding is calculated as the difference between the total and the non-specific bindings. The activity of the compounds is calculated from the specific binding and from the binding measured in the presence of the antagonist molecule.

The activity of the compounds is characterized with the IC$_{50}$ value.

B.) Investigation of Ca$^{2+}$ Mobilization in hCCR3-RBL and hCCR3 K562 Cells

HCCR3-K562 and hCCE3-RBL2H3 cells in 40,000 cells/well density (number of cells in one well of the microplate) are cultured for 24 hours. The cells are washed and loaded with calcium indicator dye (Calcium Plus assay Kit, Molecular Devices). The cells are incubated in the presence of the dye for 60 minutes while loading takes place. The dye is a fluorescent calcium indicator, which sensitively indicates the intracellular calcium concentration. The intracellular calcium concentration is in direct ratio with the fluorescent signal of the sample. The experiments are performed in a BMG NOVOSTAR apparatus, at excitation and emission wavelengths.

The selective agonists used in the experiments are:
Eotaxin
Eotaxin-2
Eotaxin-3
RANTES Following the addition of the selective agonist, the intracellular calcium concentration in the cells significantly increases which can be monitored with the help of the fluorescent signal. In the experiments an agonist concentration is used which causes a 75% calcium signal compared to the maximum attainable signal.

Antagonists are added 15 minutes before the agonist treatment.

The change of the fluorescent signal is monitored for 30 seconds, during that period the process takes place.

The intensity of the maximum calcium signal following the addition of the agonist is compared with the calcium signal obtained after the addition of the same agonist, but in the presence of the inhibitor.

The activity of the compounds is characterized with the $IC_{50}$ values.

On the basis of tests A and B the compounds of general formula (I) and (IA) were found biologically active.

The compounds of general formula (I) and (IA) according to claim 5 which form a narrower group of the compounds of general formula (I) and (IA) of claim 1 were found the most potent. The $IC_{50}$ values of these compounds were below 200 nM. Most of the compounds had $IC_{50}$ values were below 50 nM. A number of compounds exhibited $IC_{50}$ values below 5 nM.

For example, of the compounds of general formula (I) or (IA), those described in certain Examples exhibited the following $IC_{50}$ values, as determined in test B:

| Example: | $IC_{50}$ [nM] |
|---|---|
| 9. | 3.9 |
| 17. | 1.9 |
| 20. | 13 |
| 23. | 13 |
| 2. | 18 |
| 3. | 5 |
| 4. | 3.4 |
| 5. | 0.9 |
| 11. | 1.6 |
| 14. | 1 |
| 15. | 0.9 |
| 16. | 0.3 |
| 18. | 0.95 |
| 21. | 82.5 |

What is claimed is:
1. A compound of formula (I) or (IA),

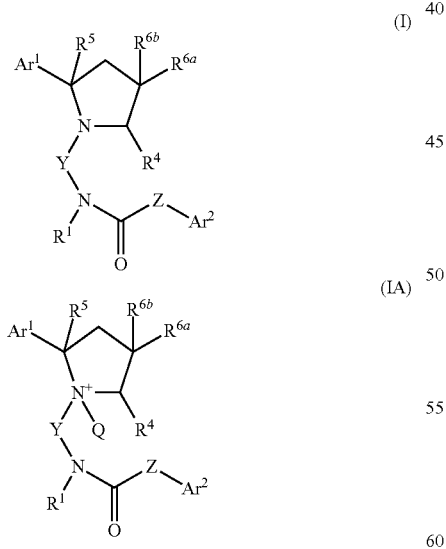

wherein
Ar$^1$ represents a phenyl or naphthyl group, optionally substituted with one or more identical or non-identical, straight or branched $C_{1-4}$ alkyl groups, straight or branched $C_{1-4}$ alkoxy groups, halogen atoms, trifluoromethyl groups, cyano groups, nitro groups, hydroxyl groups, $C_{1-2}$ alkylenedioxy groups, amino groups, or amino groups substituted with one or two identical or non-identical, straight or branched $C_{1-4}$ alkyl groups;

R$^1$, represents a hydrogen atom, or a straight or branched $C_{1-4}$ alkyl group;

R$^4$, R$^5$, R$^{6a}$, R$^{6b}$ each represents a hydrogen atom, or
R$^4$ stands for a straight or branched $C_{1-4}$ alkyl group and R$^5$, R$^{6a}$ and R$^{6b}$ each represents a hydrogen atom, or
R$^5$ stands for a straight or branched $C_{1-4}$ alkyl group and R$^4$, R$^{6a}$ and R$^{6b}$ each represent a hydrogen atom, or
R$^{6a}$ stands for a straight or branched $C_{1-4}$ alkyl group, R$^{6b}$ stands for a straight or branched $C_{1-4}$ alkyl group or a hydrogen atom, and each of R$^5$ and R$^4$ represents a hydrogen atom;

Y, Z each independently represents a straight $C_{1-4}$ alkylene group, optionally substituted with one or more identical or non-identical, straight or branched $C_{1-4}$ alkyl groups;

Ar$^2$ represents a phenyl, thienyl, or furyl group, optionally substituted with one or more identical or non-identical, straight or branched $C_{1-4}$ alkyl groups, straight or branched $C_{1-4}$ alkoxy groups, halogen atoms, hydroxyl groups, cyano groups, nitro groups, trifluoromethyl groups, $C_{1-2}$ alkylenedioxy groups, amino groups, or amino groups substituted with one or two identical or non-identical, straight or branched $C_{1-4}$ alkyl groups; or
a 5- or 6-membered heterocyclic ring containing one, two, or three nitrogen atoms, or one nitrogen atom and one oxygen atom, or one nitrogen atom and one sulfur atom, optionally substituted with one or more, identical or non-identical, straight or branched $C_{1-4}$ alkyl groups, straight or branched $C_{1-4}$ alkoxy groups, hydroxyl groups, halogen atoms, nitro groups, cyano groups, trifluoromethyl groups, $C_{1-2}$ alkylenedioxy groups, —NR$^7$R$^8$, —CONR$^7$R$^8$ or —SO$_2$NR$^7$R$^8$ groups, where R$^7$ and R$^8$ independently stand for a hydrogen atom or a straight or branched $C_{1-4}$ alkyl group, or R$^7$ and R$^8$ together with the nitrogen atom form a group of formula (a),

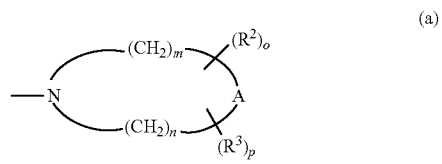

where,
R$^2$ and R$^3$ each independently represents a straight or branched $C_{1-4}$ alkyl group or a $C_{3-6}$ cycloalkyl group,
A represents a —CHR$^{12}$ group, oxygen atom, sulfur atom or —NR$^9$ group, where R$^{12}$ and R$^9$ each independently stands for a hydrogen atom, a straight or branched $C_{1-4}$ alkyl group or a $C_{3-6}$ cycloalkyl group,
m has the value of 1, 2 or 3,
n has the value of 1 or 2,
o has the value of 0 or 1, and
p has the value of 0 or 1;
or
the benzolog of a 5- or 6-membered heterocyclic ring containing one, two, or three nitrogen atoms, or one nitrogen atom and one oxygen atom, or one nitrogen atom and one sulfur atom, optionally substituted with one or more identical or non-identical straight or branched C$_{1-4}$ alkyl groups, straight or branched C$_{1-4}$ alkoxy groups, hydroxyl groups, halogen atoms, trifluoromethyl groups, nitro groups, cyano groups, C$_{1-2}$ alkylenedioxy groups, or —NR$^7$R$^8$, —CONR$^7$R$^8$ or —SO$_2$NR$^7$R$^8$ groups, where the meanings of R$^7$ and R$^8$ are as defined above; or a 5- or 6-membered heterocyclic ring containing one, two, or three nitrogen atoms, or one nitrogen atom and one oxygen atom, or one nitrogen atom and one sulfur atom, condensed with a heteroaromatic 6-membered ring containing one or two nitrogen atoms, optionally substituted with one or more identical or non-identical, straight or branched C$_{1-4}$ alkyl groups, straight or branched C$_{1-4}$ alkoxy groups, hydroxyl groups, halogen atoms, nitro groups, cyano groups, trifluoromethyl groups, C$_{1-2}$ alkylenedioxy groups, or —NR$^7$R$^8$, —CONR$^7$R$^8$ or —SO$_2$NR$^7$R$^8$ groups, where the meanings of R$^7$ and R$^8$ are as defined above; and Q represents an —O$^-$ group, or an —N$^-$—H or —N$^-$—CO—R$^{10}$ group, where R$^{10}$ stands for a hydrogen atom, a straight or branched C$_{1-4}$ alkyl group, a C$_{3-6}$ cycloalkyl group, or a phenyl-, benzyl- or —NH—R$^{11}$ group, where R$^{11}$ represents a straight or branched C$_{1-4}$ alkyl group, a C$_{3-6}$ cycloalkyl group, or a phenyl- or benzyl- group-;

or a salt thereof.

2. A compound according to claim 1,
wherein
Ar$^1$ represents a phenyl or naphthyl group, optionally substituted with one or more identical or non-identical, straight or branched C$_{1-4}$ alkyl groups, straight or branched C$_{1-4}$ alkoxy groups, halogen atoms, trifluoromethyl groups, cyano groups, nitro groups, hydroxyl groups, C$_{1-2}$ alkylenedioxy groups, amino groups, or amino groups substituted with one or two identical or non-identical, straight or branched C$_{1-4}$ alkyl groups;
R$^1$, represents a hydrogen atom, or a straight or branched C$_{1-4}$ alkyl group;
R$^4$, R$^5$, R$^{6a}$, R$^{6b}$ each represents a hydrogen atom, or
R$^4$ stands for a straight or branched C$_{1-4}$ alkyl group, and R$^5$, R$^{6a}$ and R$^{6b}$ each represents a hydrogen atom, or
R$^5$ stands for a straight or branched C$_{1-4}$ alkyl group, and R$^4$, R$^{6a}$ and R$^{6b}$ each represents a hydrogen atom, or
R$^{6a}$ stands for a straight or branched C$_{1-4}$ alkyl group, R$^{6b}$ stands for a straight or branched C$_{1-4}$ alkyl group or a hydrogen atom, and R$^5$ and R$^4$ each represents a hydrogen atom;
Y, Z each independently represents a straight C$_{1-4}$ alkylene group, optionally substituted with one or more identical or non-identical, straight or branched C$_{1-4}$ alkyl groups;
Ar$^2$ represents a phenyl, thienyl, or furyl group, optionally substituted with one or more identical or non-identical, straight or branched C$_{1-4}$ alkyl groups, straight or branched C$_{1-4}$ alkoxy groups, halogen atoms, hydroxyl groups, cyano groups, nitro groups, trifluoromethyl groups, C$_{1-2}$ alkylenedioxy groups, amino groups, or amino groups substituted with one or two identical or non-identical, straight or branched C$_{1-4}$ alkyl groups; or a 5- or 6-membered heterocyclic ring containing one, two, or three nitrogen atoms, or one nitrogen atom and one oxygen atom, or one nitrogen atom and one sulfur atom, optionally substituted with one or more identical or non-identical, straight or branched C$_{1-4}$ alkyl groups, straight or branched C$_{1-4}$ alkoxy groups, hydroxyl groups, halogen atoms, nitro groups, cyano groups, trifluoromethyl groups, C$_{1-2}$ alkylenedioxy groups, or —NR$^7$R$^8$, —CONR$^7$R$^8$ or —SO$_2$NR$^7$R$^8$ groups, where R$^7$ and R$^8$ each independently stands for a hydrogen atom or a straight or branched C$_{1-4}$ alkyl group, or R$^7$ and R$^8$ together with the nitrogen atom form a group of formula (a),

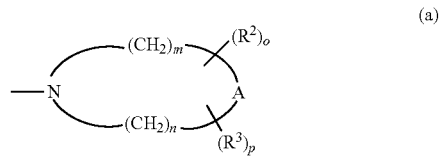

where,
R$^2$ and R$^3$ each independently represents a straight or branched C$_{1-4}$ alkyl group or a C$_{3-6}$ cycloalkyl group,
A represents a —CHR$^{12}$ group, oxygen atom, sulfur atom or —NR$^9$ group, where R$^{12}$ and R$^9$ each independently stands for a hydrogen atom, a straight or branched C$_{1-4}$ alkyl group or a C$_{3-6}$ cycloalkyl group,
m has the value of 1, 2 or 3,
n has the value of 1 or 2,
o has the value of 0 or 1, and
p has the value of 0 or 1,
or
the benzolog of a 5- or 6-membered heterocyclic ring containing one, two, or three nitrogen atoms, or one nitrogen atom and one oxygen atom, or one nitrogen atom and one sulfur atom, optionally substituted with one or more, identical or non-identical, straight or branched C$_{1-4}$ alkyl groups, straight or branched C$_{1-4}$ alkoxy groups, hydroxyl groups, halogen atoms, trifluoromethyl groups, nitro groups, cyano groups, C$_{1-2}$ alkylenedioxy groups, or —NR$^7$R$^8$, —CONR$^7$R$^8$ or —SO$_2$NR$^7$R$^8$ groups, where the meaning of R$^7$ and R$^8$ are as defined above; or a 5- or 6-membered heterocyclic ring containing one, two, or three nitrogen atoms, or one nitrogen atom and one oxygen atom, or one nitrogen atom and one sulfur atom, condensed with a heteroaromatic 6-membered ring containing one or two nitrogen atoms, optionally substituted with one or more, identical or non-identical, straight or branched C$_{1-4}$ alkyl groups, straight or branched C$_{1-4}$ alkoxy groups, hydroxyl groups, halogen atoms, nitro groups, cyano groups, trifluoromethyl groups, C$_{1-2}$ alkylenedioxy groups, or —NR$^7$R$^8$, —CONR$^7$R$^8$ or —SO$_2$NR$^7$R$^8$ groups, where the meanings of R$^7$ and R$^8$ are as defined above; and Q represents an —N$^-$—H group;
or a salt thereof.

3. A compound according to claim 1,
wherein
Ar$^1$ represents a phenyl or naphthyl group, optionally substituted with one or more identical or non-identical, straight or branched C$_{1-4}$ alkyl groups, straight or branched C$_{1-4}$ alkoxy groups, or halogen atoms;
R$^1$ represents a hydrogen atom, or a methyl group;
R$^4$, R$^5$, K R$^{6b}$ each represents a hydrogen atom, or
R$^4$ stands for a methyl group and R$^5$, R$^{6a}$ and R$^{6b}$ each represents a hydrogen atom, or $R^{6a}$ stands for a methyl group, $R^{6b}$ stands for a methyl group or a hydrogen atom, and $R^5$ and $R^4$ each represents a hydrogen atom;

Y, Z each independently represents a straight $C_{1-4}$ alkylene group, optionally substituted with one or more identical or non-identical, straight or branched $C_{1-4}$ alkyl groups;

$Ar^2$ represents the benzolog of a 5- or 6-membered heterocyclic ring containing one, two, or three nitrogen atoms, or one nitrogen atom and one oxygen atom, or one nitrogen atom and one sulfur atom, optionally substituted with one or more identical or non-identical, straight or branched $C_{1-4}$ alkyl groups, straight or branched $C_{1-4}$ alkoxy groups, hydroxyl groups, halogen atoms, trifluoromethyl groups, nitro groups, cyano groups, $C_{1-2}$ alkylenedioxy groups, or —$NR^7R^8$, —$CONR^7R^8$ or —$SO_2NR^7R^8$ groups, where $R^7$ and $R^8$ each independently stands for a hydrogen atom or a straight or branched $C_{1-4}$ alkoxy group, or $R^7$ and $R^8$ together with the nitrogen atom form a group of the formula (a),

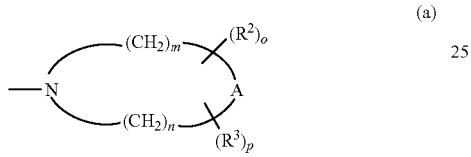

(a)

where,
$R^2$ and $R^3$ each independently represents a straight or branched $C_{1-4}$ alkyl group or a $C_{3-6}$ cycloalkyl group,
A represents a —$CHR^{12}$ group, oxygen atom, sulfur atom or —$NR^9$ group, where $R^{12}$ and $R^9$ each independently stands for a hydrogen atom, a straight or branched $C_{1-4}$ alkyl group or a $C_{3-6}$ cycloalkyl group,
m has the value of 1, 2 or 3,
n has the value of 1 or 2,
o has the value of 0 or 1, and
p has the value of 0 or 1, or
a 5- or 6-membered heterocyclic ring containing one, two, or three nitrogen atoms, or one nitrogen atom and one oxygen atom, or one nitrogen atom and one sulfur atom, condensed with a heteroaromatic 6-membered ring containing one or two nitrogen atoms, optionally substituted with one or more identical or non-identical, straight or branched $C_{1-4}$ alkyl groups, straight or branched $C_{1-4}$ alkoxy groups, hydroxyl groups, halogen atoms, nitro groups, cyano groups, trifluoromethyl groups, $C_{1-2}$ alkylenedioxy groups, or —$NR^7R^8$, —$CONR^7R^8$ or —$SO_2NR^7R^8$ groups, where the meanings of $R^7$ and $R^8$ are as defined above; and Q represents an —$O^-$ group, —$N^-$—H or —$N^-$—CO—$R^{10}$ group, where $R^{10}$ stands for a hydrogen atom, a straight or branched $C_{1-4}$ alkyl group, a $C_{3-6}$ cycloalkyl group, or a phenyl, benzyl or —NH—$R^{11}$ group, where $R^{11}$ represents a straight or branched $C_{1-4}$ alkyl group, $C_{3-6}$ cycloalkyl group, phenyl- or benzyl-group-;
or a salt thereof.

4. A compound according to claim 1,
wherein
$Ar^1$ represents a phenyl group, optionally substituted with one or more identical or non-identical halogen atoms;
$R^1$ represents a hydrogen atom;
$R^4$, $R^5$, $R^{6a}$, $R^{6b}$ each represents a hydrogen atom;

Y, Z each independently represents a straight $C_{1-4}$ alkylene group, optionally substituted with one or more identical or non-identical, straight or branched $C_{1-4}$ alkyl groups;

$Ar^2$ represents the benzolog of a 5- or 6-membered heterocyclic ring containing one nitrogen atom and one sulfur atom, optionally substituted with one or more, identical or non-identical, straight or branched $C_{1-4}$ alkyl groups, or 5- or 6-membered heterocyclic ring containing one nitrogen atom and one sulfur atom, condensed with a heteroaromatic 6-membered ring containing one or two nitrogen atoms, optionally substituted with one or more identical or non-identical, straight or branched $C_{1-4}$ alkyl groups, straight or branched $C_{1-4}$ alkoxy groups, or a —$NR^7R^8$ group, where $R^7$ and $R^8$ each independently stands for a hydrogen atom, or a straight or branched $C_{1-4}$ alkyl group, or $R^7$ and $R^8$ together with the nitrogen atom form a group of the formula (a);

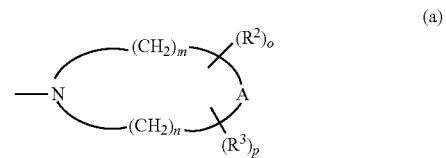

(a)

where,
$R^2$ and $R^3$ each independently represents a straight or branched $C_{1-4}$ alkyl group or a $C_{3-6}$ cycloalkyl group,
A represents a —$CHR^{12}$ group, oxygen atom, sulfur atom or —$NR^9$ group, where $R^{12}$ and $R^9$ each independently stands for a hydrogen atom, a straight or branched $C_{1-4}$ alkyl group or a $C_{3-6}$ cycloalkyl group-,
m has the value of 1, 2 or 3,
n has the value of 1 or 2,
o has the value of 0 or 1, and
p has the value of 0 or 1; and
Q represents a —$O^-$ group, or a —$N^-$—H or —$N^-$—CO—$R^{10}$ group, where $R^{10}$ stands for a hydrogen atom or a straight or branched $C_{1-4}$ alkyl group, or a —NH—$R^{11}$ group, where $R^{11}$ represents a straight or branched $C_{1-4}$ alkyl group;
or a salt thereof.

5. A compound according to claim 1,
wherein
$Ar^1$ represents a phenyl group substituted with one or two identical or non-identical halogen atoms,
or a salt thereof.

6. A compound according to claim 1 selected from the group consisting of:
N-{3-[2-(3,4-dichlorophenyl)pyrrolidin-1-yl]propyl}-3-(5-methoxy[1,3]thiazolo[5,4-b]pyridin-2-yl)propionamide,
N-{3-[2-(3,4-dichlorophenyl)pyrrolidin-1-yl]propyl}-3-(5-(methylamino) [1,3]thiazolo[5,4-b]pyridin-2-yl)propionamide,
N-{3-[2-(3,4-dichlorophenyl)pyrrolidin-1-yl]propyl}-3-(5-pyrrolidin-1-yl[1,3]thiazolo[5,4-b]pyridin-2-yl)propionamide,
N-{3-[2-(3,4-dichlorophenyl)pyrrolidin-1-yl]propyl}-3-(5-piperidin-1-yl[1,3]thiazolo[5,4-b]pyridin-2-yl)propionamide, N-{3-[2-(3,4-dichlorophenyl)pyrrolidin-1-yl]propyl}-3-(5-morpholin-4-yl[1,3]thiazolo[5,4-b]pyridin-2-yl)propionamide,
N-{3-[2-(3,4-dichlorophenyl)pyrrolidin-1-yl]propyl}-3-(5-methyl[1,3]thiazolo[5,4-b]pyridin-2-yl)propionamide,
N-{3-[2-(3,4-dichlorophenyl)pyrrolidin-1-yl]propyl}-3-(5-(4-methylpiperazin-1-yl)[1,3]thiazolo[5,4-b]pyridin-2-yl)propionamide,
N-{3-[2-(3,4-dichlorophenyl)pyrrolidin-1-yl]propyl}-3-(6-methyl-1,3-benzothiazol-2-yl)propionamide,
N-{3-[2-(3,4-dichlorophenyl)pyrrolidin-1-yl]propyl}-3-(5-(2,6-dimethylmorpholin-4-yl)[1,3]thiazolo[5,4-b]pyridin-2-yl)propionamide,
N-{3-[2-(3,4-dichlorophenyl)pyrrolidin-1-yl]propyl}-3-(6-piperidin-1-yl)[1,3]thiazolo[4,5-b]pyrazin-2-yl)propionamide,
N-{3-[2-(3,4-dichlorophenyl)pyrrolidin-1-yl]propyl}-3-(6-morpholin-4-yl)[1,3]thiazolo[4,5-b]pyrazin-2-yl)propionamide,
N-(3-[2-(3,4-dichlorophenyl)pyrrolidin-1-yl]-1-methylpropyl)-3-(5-morpholin-4-yl[1,3]thiazolo[5,4-b]pyridin-2-yl)]propionamide,
N-(3-[2-(3,4-dichlorophenyl)pyrrolidin-1-yl]-1-methylpropyl)-3-(5-piperidin-1-yl[1,3]thiazolo[5,4-b]pyridin-2-yl)]propionamide,
1-amino-2-(3,4-dichlorophenyl)-1-(3-{[3-(5-pyrrolidin-1-yl[1,3]thiazolo[4,5-b]pyridin-2-yl)propanoyl]amino} propyl)pyrrolidinium tosylate,
1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-morpholin-4-yl[1,3]thiazolo[4,5-b]pyridin-2-yl)propanoyl]amino} propyl)pyrrolidinium tosylate,
1-amino-2-(3,4-dichlorophenyl)-1-(3-{[3-(5-methyl[1,3]thiazolo[4,5-b]pyridin-2-yl)propanoyl]amino} propyl)pyrrolidinium tosylate,
1-amino-2-(3,4-dichlorophenyl)-1-[3-({3-(5-(2,6-dimethylmorpholin-4-yl)[1,3]thiazolo[4,5-b]pyridin-2-yl)propanoyl]amino}propyl)pyrrolidinium tosylate,
N-{3-[2-(3,4-dichlorophenyl)-1-oxidopyrrolidin-1-yl]propyl}-3-(5-piperidin-1-yl)[1,3]thiazolo[4,5-b]pyridin-2-yl)propionamide,
N-{3-[2-(3,4-dichlorophenyl)-1-oxidopyrrolidin-1-yl]propyl}-3-(5-morpholin-4-yl[1,3]thiazolo[4,5-b]pyridin-2-yl)propionamide,
N-{3-[2-(3,4-dichlorophenyl)-1-oxidopyrrolidin-1-yl]propyl}-3-(5-pyrrolidin-1-yl[1,3]thiazolo[4,5-b]pyridin-2-yl)propionamide, and
1-(Acetylamino)-2-(3,4-dichlorophenyl)-1-(3-{[3-(5-piperidin-1-yl[1,3]thiazolo[4,5-b]pyridin-2-yl)propanoyl]amino}propyl)pyrrolidinium hydrochloride
or a salt thereof.

7. A compound according to claim 6 selected from the group consisting of:
N-{3-[2-(3,4-dichlorophenyl)pyrrolidin-1-yl]propyl}-3-(5-(methylamino)[1,3]thiazolo[5,4-b]pyridin-2-yl)propionamide,
N-{3-[2-(3,4-dichlorophenyl)pyrrolidin-1-yl]propyl}-3-(5-pyrrolidin-1-yl[1,3]thiazolo[5,4-b]pyridin-2-yl)propionamide,
N-{3-[2-(3,4-dichlorophenyl)pyrrolidin-1-yl]propyl}-3-(5-piperidin-1-yl[1,3]thiazolo[5,4-b]pyridin-2-yl)propionamide,
N-{3-[2-(3,4-dichlorophenyl)pyrrolidin-1-yl]propyl}-3-(5-morpholin-4-yl[1,3]thiazolo[5,4-b]pyridin-2-yl)propionamide,
N-{3-[2-(3,4-dichlorophenyl)pyrrolidin-1-yl]propyl}-3-(5-(2,6-dimethylmorpholin-4-yl) [1,3]thiazolo[5,4-b]pyridin-2-yl)propionamide,
1-amino-2-(3,4-dichlorophenyl)-1-(3-{[3-(5-pyrrolidin-1-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-piperidin-1-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-morpholin-4-yl[1,3]thiazolo[4,5-b]pyridin-2-yl)propanoyl]amino}propyl)pyrrolidinium tosylate,
1-amino-2-(3,4-dichlorophenyl)-1-(3-{[3-(5-methyl[1,3]thiazolo[4,5-b]pyridin-2-yl)propanoyl]amino}propyl)pyrrolidinium tosylate,
1-amino-2-(3,4-dichlorophenyl)-1-[3-({3-(5-(2,6-dimethylmorpholin-4-yl) [1,3]thiazolo[4,5-b]pyridin-2-yl)propanoyl]amino}propyl)pyrrolidinium tosylate, and
N-{3-[2-(3,4-dichlorophenyl)-1-oxidopyrrolidin-1-yl]propyl}-3-(5-morpholin-4-yl[1,3 thiazolo[4,5-b]pyridin-2-yl)propionamide,
or a salt thereof.

8. A compound of formula (IA) according to claims 3, where,
Q represents an —$N^-$—H group or a salt thereof.

9. A process for preparing a compound of formula (I) or (IA) as set forth in claim 1, or a salt thereof,

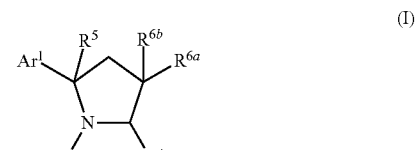

(I)

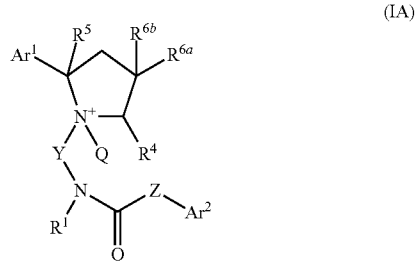

(IA)

where the meanings of $Ar^1$, $R^1$, $R^4$, $R^5$, $R^{6a}$, $R^{6b}$, Y, Z, $Ar^2$ and Q are as defined in claim 1, the process comprising a.) for preparing a compound of formula (I), reacting a compound of formula (IV),

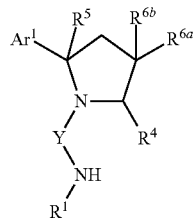

with a carboxylic acid derivative of formula (V),

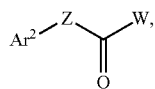

where W represents a halogen atom, hydroxyl group, —O($C_{1-4}$ alkyl) group or —OCO—Z—$Ar^2$ group; or b.) for preparing a compound of formula (I), reacting an amino compound of the formula (VI)

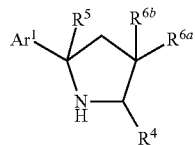

with a halogen compound of the formula (VII)

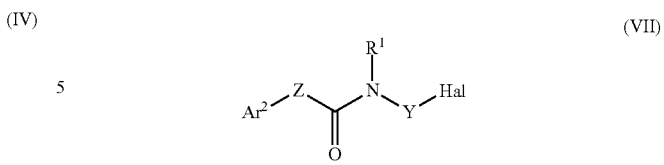

where Hal represents halogen atom; or c.) to prepare the a compound of formula (IA), wherein Q represents —O⁻ group, oxidizing a compound of formula (I) prepared by method a.) or b.) above; or d.) to prepare a compound of formula (IA), or a salt thereof, where Q represents an —N⁻—H group, further reacting a compound of formula (I) prepared by method a.) or b.) above with O-tosylhydroxylamine; or e.) to prepare a compound of formula (IA), or a salt thereof, where Q represents an —N⁻—CO—$R^{10}$ group, where $R^{10}$ represents a hydrogen atom, straight or branched $C_{1-4}$ alkyl group, $C_{3-6}$ cycloalkyl group, phenyl or benzyl group, acylating a compound of formula (IA), prepared by method d.) above, with a group of formula Hlg-CO—$R^{10}$, where Hlg represents a halogen atom; or f.) to prepare the a compound of formula (IA) where Q represents an —N⁻—CO—$R^{10}$ group, in which $R^{10}$ represents an —NH—$R^{11}$ group, reacting a compound of formula (IA) prepared by method d.) above with a compound of the formula $R^{11}$NCO.

10. A pharmaceutical composition comprising one or more compounds according to claim 1, or a salt thereof, and one or more pharmaceutically acceptable excipients.

11. A method for the treatment of asthma, allergic rhinitis, atopic dermatitis, eczema, inflammatory bowel disease, ulcerative colitis, Crohn's disease, allergic conjunctivitis, multiple sclerosis, or HIV infection, the method comprising administering to a patient in need thereof an effective dose of a compound as claimed in claim 1, or a salt thereof.

* * * * *

UNITED STATES PATENT AND TRADEMARK OFFICE
CERTIFICATE OF CORRECTION

PATENT NO. : 8,420,636 B2  
APPLICATION NO. : 13/014145  
DATED : April 16, 2013  
INVENTOR(S) : Agnes Behr et al.

Page 1 of 1

It is certified that error appears in the above-identified patent and that said Letters Patent is hereby corrected as shown below:

In the Claims

In column 32, line 65, in claim 3, delete "K" and insert -- $R^{6a}$, --, therefor.

In column 32, line 68, in claim 3, below "or" insert -- $R^5$ stands for a methyl group and $R^4$, $R^{6a}$ and $R^{6b}$ each represents a hydrogen atom, or --.

Signed and Sealed this  
Twenty-sixth Day of November, 2013

Margaret A. Focarino  
*Commissioner for Patents of the United States Patent and Trademark Office*